(12) United States Patent
Yedgar

(10) Patent No.: US 8,859,524 B2
(45) Date of Patent: Oct. 14, 2014

(54) LIPID CONJUGATES IN THE TREATMENT OF CHRONIC RHINOSINUSITIS

(75) Inventor: Saul Yedgar, Jerusalem (IL)

(73) Assignee: Yissum Research Development Company of The Hebrew University of Jerusalem, Jerusalem (IL)

( * ) Notice: Subject to any disclaimer, the term of this patent is extended or adjusted under 35 U.S.C. 154(b) by 104 days.

(21) Appl. No.: 13/283,020

(22) Filed: Oct. 27, 2011

(65) Prior Publication Data

US 2012/0071442 A1    Mar. 22, 2012

Related U.S. Application Data

(63) Continuation-in-part of application No. 11/285,375, filed on Nov. 23, 2005, now Pat. No. 8,076,312, which is a continuation-in-part of application No. PCT/IL2005/001225, filed on Nov. 17, 2005, application No. 13/283,020, which is a continuation-in-part of application No. 12/463,792, filed on May 11, 2009, now abandoned, and a continuation-in-part of application No. 12/997,014, filed as application No. PCT/US2010/034317 on May 11, 2010.

(60) Provisional application No. 61/177,083, filed on May 11, 2009.

(51) Int. Cl.
   - *A61K 31/728* (2006.01)
   - *A61K 31/685* (2006.01)
   - *A61K 31/727* (2006.01)
   - *A61K 31/717* (2006.01)

(52) U.S. Cl.
   CPC ............ *A61K 31/728* (2013.01); *A61K 31/727* (2013.01); *A61K 31/685* (2013.01); *A61K 31/717* (2013.01)
   USPC .......................................................... 514/54

(58) Field of Classification Search
   None
   See application file for complete search history.

(56) References Cited

U.S. PATENT DOCUMENTS

| | | |
|---|---|---|
| 4,604,376 A | 8/1986 | Teng |
| 4,624,919 A | 11/1986 | Kokusho et al. |
| 4,654,327 A | 3/1987 | Teng |
| 5,064,817 A | 11/1991 | Yedgar et al. |
| 5,169,636 A | 12/1992 | Nanba et al. |
| 5,354,853 A | 10/1994 | Staveski et al. |
| 5,401,511 A | 3/1995 | Margalit |
| 5,401,777 A | 3/1995 | Ammon et al. |
| 5,464,942 A | 11/1995 | Sakurai et al. |
| 5,470,578 A | 11/1995 | Aoki et al. |
| 5,512,671 A | 4/1996 | Piantadosi et al. |
| 5,587,363 A | 12/1996 | Henderson |
| 5,707,821 A | 1/1998 | Rydel et al. |
| 5,733,892 A | 3/1998 | Sakurai et al. |
| 5,785,975 A | 7/1998 | Parikh |
| 6,022,866 A | 2/2000 | Falk et al. |
| 6,043,231 A | 3/2000 | Pruzanski et al. |
| 6,071,532 A | 6/2000 | Chaikof et al. |
| 6,162,787 A | 12/2000 | Sorgente et al. |
| 6,171,614 B1 | 1/2001 | Chaikof et al. |
| 6,180,596 B1 | 1/2001 | Tsao |
| 6,325,385 B1 | 12/2001 | Iwashita et al. |
| 6,749,813 B1 | 6/2004 | David et al. |
| 7,034,006 B2 | 4/2006 | Yedgar et al. |
| 7,101,859 B2 | 9/2006 | Yedgar et al. |
| 7,141,552 B2 | 11/2006 | Yedgar et al. |
| 7,393,938 B2 | 7/2008 | Yedgar |
| 7,504,384 B2 | 3/2009 | Yedgar et al. |
| 7,608,598 B2 | 10/2009 | Yedgar |
| 2002/0049183 A1 | 4/2002 | Yedgar et al. |
| 2004/0087492 A1 | 5/2004 | Yedgar |
| 2004/0229842 A1 | 11/2004 | Yedgar et al. |
| 2006/0293276 A1 | 12/2006 | Yedgar et al. |
| 2007/0185052 A1 | 8/2007 | Yedgar et al. |

FOREIGN PATENT DOCUMENTS

| | | |
|---|---|---|
| EP | 0236951 | 9/1987 |
| EP | 0529659 | 3/1993 |
| EP | 0581281 | 2/1994 |
| EP | 0581282 B | 2/1994 |
| EP | 1046394 | 10/2000 |
| JP | 04082893 | 3/1992 |
| JP | 09030979 | 2/1997 |
| JP | 2002345455 | 12/2002 |
| JP | 2003160498 | 3/2003 |
| JP | 2003335801 | 11/2003 |
| JP | 2004018841 | 1/2004 |
| JP | 2004170194 | 6/2004 |

(Continued)

OTHER PUBLICATIONS

Extended European Search Report of European Application No. 05808267.8 issued Mar. 15, 2012.
Phyllis, Dan et al., "Inhibition of Type I and Type II Phospholipase A2 by Phosphatidyl-Ethanolamine Linked to Polymeric Carriers," Biochemistry, 1998, 37 (17), pp. 6199-6204.
International Search Report for International Application No. PCT/IL2012/050423 dated Mar. 25, 2013.

(Continued)

*Primary Examiner* — Kamal Saeed
(74) *Attorney, Agent, or Firm* — Mark S. Cohen; Pearl Cohen Zedek Latzer Baratz LLP

(57) ABSTRACT

This invention provides a method of treating, suppressing, inhibiting, or preventing chronic rhinosinusitis in a subject comprising the step of administering to a subject a compound comprising a lipid or phospholipid moiety bond to a physiologically acceptable monomer, dimer, oligomer, or polymer, and/or a pharmaceutically acceptable salt or a pharmaceutical product thereof. This invention also provides a method of treating, suppressing, inhibiting, or preventing nasal polyps in a subject comprising the step of administering to a subject a compound comprising a lipid or phospholipid moiety bond to a physiologically acceptable monomer, dimer, oligomer, or polymer, and/or a pharmaceutically acceptable salt or a pharmaceutical product thereof.

20 Claims, 3 Drawing Sheets

(56) References Cited

FOREIGN PATENT DOCUMENTS

| | | |
|---|---|---|
| WO | WO 87/02777 | 5/1987 |
| WO | WO 91/00289 | 1/1991 |
| WO | WO 96/04001 | 2/1996 |
| WO | WO 96/11670 | 4/1996 |
| WO | WO 96/28544 | 9/1996 |
| WO | WO 97/01330 | 1/1997 |
| WO | WO 97/48337 | 12/1997 |
| WO | WO 98/16198 | 4/1998 |
| WO | WO 98/51285 | 11/1998 |
| WO | WO 01/51003 | 7/2001 |
| WO | WO 01/91805 | 12/2001 |
| WO | WO 2005/084307 | 9/2005 |

OTHER PUBLICATIONS

Riviere, K. Investigation of the Enhancement of Drug Synergy by Co-Delivery in Targeted Liposomes, 2009, Dissertation.

Ehehalt, R. et al., "Lipid Based Therapy for Ulcerative Colitis—Modulation of Intestinal Mucus Membrane Phospholipids as a Tool to Influence Inflammation," Int. J. Mol. Sci. 2010, 11, 4149-4164.

Office Action for Japanese Patent Application No. 2001-551427 dated Nov. 20, 2009.

Mexican Office Action for Mexican Patent Application No. MX/a2008/001639 dated May 2, 2013.

Albini, A, Iwamoto, Y, Kleinman, HK, Martin, GR, Aaronson, SA, Kozlowski, JM and McEwan, RN (1987) "A rapid in vitro assay for quantitating the invasive potential of tumor cells" *Cancer Res* 47(12):3239-45.

Balsinde, J, Balboa, MA, Yedgar, S and Dennis, EA (2000) "Group V phospholipase A(2)-mediated oleic acid mobilization in lipopolysac-charide-stimulated P388D(1) macrophages" *J Biol Chem* 275(7):4783-6.

Beck, G, Yard, BA, Schulte, J, Oberacker, R, Van Ackern, K, Van Der Woude, FJ, Krimsky, M, Kaszkin, M and Yedgar, S (2002) "Inhibition of LPS-induced chemokine production in human lung endothelial cells by lipid conjugates anchored to the membrane" *Br J Pharmacol* 135(7):1665-74.

Cabanas, C and Hogg, N (1993) "Ligand intercellular adhesion molecule 1 has a necessary role in activation of integrin lymphocyte function-associated molecule 1" *Proc Natl Acad Sci U S A* 90(12):5838-42.

Chen, WM, Soria, J, Soria, C, Krimsky, M and Yedgar, S (2002) "Control of capillary formation by membrane-anchored extracellular inhibitor of phospholipase A(2)" *FEBS Lett* 522(1-3):113-8.

Dan, P, Dagan, A, Krimsky, M, Pruzanski, W, Vadas, P. and Yedgar, S (1998) "Inhibition of type I and type II phospholipase A2 by phosphatidyl-ethanolamine linked to polymeric carriers" *Biochemistry* 37(17):6199-204.

Darville, T, Yedgar, S, Krimsky, M, Andrews, CW, Jr., Jungas, T and Ojcius, DM (2004) "Protection against *Chlamydia trachomatis* infection in vitro and modulation of inflammatory response in vivo by membrane-bound glycosaminoglycans" *Microbes Infect* 6(4):369-76.

Greaves MW and Camp RD (1988) "Prostaglandins, leukotrienes, phospholipase, platelet activating factor, and cytokines: an integrated approach to inflammation of human skin." *Arch Dermatol Res* 280:S33-41.

Krimsky, M, Dagan, A, Aptekar, L, Ligumsky, M and Yedgar, S (2000) "Assessment of intestinal permeability in rats by permeation of inulin-fluorescein" *J Basic Clin Physiol Pharmacol* 11(2):143-53.

Krimsky, M, Yedgar, S, Aptekar, L, Schwob, O, Goshen, G, Gruzman, A, Sasson, S and Ligumsky, M (2003) "Amelioration of TNBS-induced colon inflammation in rats by phospholipase A2 inhibitor" *Am J Physiol Gastrointest Liver Physiol* 285(3):G586-92.

Margolis-Nunno, H, Ben-Hur, E, Gottlieb, P, Robinson, R, Oetjen, J and Horowitz, B (1996) "Inactivation by phthalocyanine photosensitization of multiple forms of human immunodeficiency virus in red cell concentrates" *Transfusion* 36(8):743-50.

Murthy, SN, Cooper, HS, Shim, H, Shah, RS, Ibrahim, SA and Sedergran, DJ (1993) "Treatment of dextran sulfate sodium-induced murine colitis by intracolonic cyclosporin" *Dig Dis Sci* 38(9):1722-34.

Okayasu, I, Hatakeyama, S, Yamada, M, Ohkusa, T, Inagaki, Y and Nakaya, R (1990) "A novel method in the induction of reliable experimental acute and chronic ulcerative colitis in mice" *Gastroenterology* 98(3):694-702.

Schmiel, DH and Miller, VL (1999) "Bacterial phospholipases and pathogenesis" *Microbes Infect* 1(13):1103-12.

Schnitzer, E, Dagan, A, Krimsky, M, Lichtenberg, D, Pinchuk, I, Shinar, H and Yedgar, S (2000) "Interaction of hyaluronic acid-linked phosphatidylethanolamine (HyPE) with LDL and its effect on the susceptibility of LDL lipids to oxidation" *Chem Phys Lipids* 104(2):149-60.

Schnitzer, E, Yedgar, S, Danino, D, Talmon, Y and Lichtenberg, D (1999) "The Interaction of hyaluronic-phosphatidylethanolamine with low density lipoprotein (LDL) and its effect on copper induced LDL oxidation" *Biophysical Journal* 76(1): Part 2.

Schnitzer, E, Pinchuk, I, Fainaru, M, Lichtenberg, D and Yedgar, S (1998) "LDL-associated phospholipase A does not protect LDL against lipid peroxidation in vitro" *Free Radic Biol Med* 24(7-8):1294-303.

Yard, BA, Yedgar, S, Scheele, M, Van Der Woude, D, Beck, G, Heidrich, B, Krimsky, M, Van Der Woude, FJ and Post, S (2002) "Modulation of IFN-gamma-induced immunogenicity by phosphatidylethanolamine-linked hyaluronic acid" *Transplantation* 73(6):984-92.

Yedgar, S, Lichtenberg, D and Schnitzer, E (2000) "Inhibition of phospholipase A(2) as a therapeutic target" *Biochim Biophys Acta* 1488(1-2):182-7.

Soeda et al., "Tissue Plasminogen Activator Catalyzed Lys-Plasminogen Activation on Heparin-Inserted Phospholipid Liposomes," Biochemistry 29:5188-5194, 1990.

Teitelbaum D, Arnon R, Sela M, Rabinsohn Y, Shapiro D., "Sphingomyelin Specific Antibodies Elicited by Synthetic Conjugates," Immunochemistry. Nov. 1973;10(11):735-43.

Weltzien HU, Matthiessen HP, Meyer-Delius M, Zimmermann F, Rude E., "Acidic "Peptidophospholipids", A New Class of Hapten-Bearing Cell Surface Modifying Reagents," Mol Immunol. Sep. 1984;21(9):801-10.

Winger TM, Ludovice PJ, Chaikof EL, "Lipopeptide Conjugates: Biomolecular Building Blocks for Receptor Activating Membrane-Mimetic Structures," Biomaterials. Feb. 1996;17(4):437-41.

Supplementary Search Report of European Application No. 05724186.1 Dated Nov. 17, 2009.

Cummings, B.S., "Phospholipase $A_2$ as targets for anti-cancer drugs," Biochemical Pharmacology 74 (2007), pp. 949-959.

Kokotos, G. et al., "Novel 2-Oxoamide Inhibitors of Human Group IVA Phospholipase A2," J. Med. Chem., 2002, 45, pp. 2891-2893.

Brenner, T, Arnon, R, Sela, M, Abramsky, O, Meiner, Z, Riven-Kreitman, R, Tarcik, N and Teitelbaum, D (2001) "Humoral and cellular immune responses to Copolymer 1 in multiple sclerosis patients treated with Copaxone" *J Neuroimmunol* 115(1-2):152-60.

Brenner, T, Lisak, RP, Rostami, A, Pleasure, DE and Silberberg, DH (1986) "Astrocytes, oligodendrocytes, and Schwann cells share a common antigenic determinant that cross-reacts with myelin basic protein: identification with monoclonal antibody" *J Neurosci* 6(7):1925-33.

Brenner, T, Poradosu, E, Soffer, D, Sicsic, C, Gazit, A and Levitzki, A (1998) "Suppression of experimental autoimmune encephalomyelitis by tyrphostin AG-556" *Exp Neurol* 154(2):489-98.

Carey et al, "Contrasting Effects of Cycloxygenase-1 (COX-1) and COX-2 Deficiency in the Host Response to Influenze, A Viral Infection". Journ. of Immunology 2005, vol. 15: 175 (10): 6878-84.

Davidson, FF, Dennis, EA, Powell, M and Glenney, Jr, Jr. (1987) "Inhibition of phospholipase A2 by "lipocortins" and calpactins. An effect of binding to substrate phospholipids" *J Biol Chem* 262(4):1698-705.

Parish et al, "Evidence That Sulphated Polysaccharides Inhibit Tumour Metastasis by Blocking Tumour-Cell-Derived Heparanases," Int. J. Cancer 40: 511-518, 1987.

(56) References Cited

OTHER PUBLICATIONS

Wang D.P, Matthias Schuster, Yi Fong Wang, Chi Huey Wong "Synthesis of Phospholipid-Inhibitor Conjugates by Enzymic Transphosphatidylation With Phospholipase", J. Am. Chem. Soc.; 1993; 115(23); 10487-10491.
Office Action for U.S. Appl. No. 10/919,523 dated Mar. 26, 2014.
Office Action for U.S. Appl. No. 12/406,130 dated Mar. 12, 2014.
International Preliminary Report Application No. PCT/IL2012/050423 Dated May 8, 2014.

LIPID CONJUGATES IN THE TREATMENT OF CHRONIC RHINOSINUSITIS

CROSS REFERENCE TO RELATED APPLICATIONS

This application is a continuation-in-part of U.S. patent application Ser. No. 11/285,375, filed Nov. 23, 2005, now U.S. Pat. No. 8,076,312, which is a continuation-in-part of PCT International Application Number PCT/IL2005/001225, filed Nov. 17, 2005. This application is also a continuation-in-part of U.S. patent application Ser. No. 12/463,792, filed May 11, 2009, now abandoned and of U.S. application Ser. No. 12/997,014, filed Dec. 9, 2010, which is a National Phase Application of PCT International Application No. PCT/US10/34317, International Filing Date May 11, 2010, claiming priority of United States Provisional Application Number 61/177,083, filed May 11, 2009, which are all hereby incorporated by reference in their entirety.

FIELD OF THE INVENTION

This invention provides a method of treating, suppressing, inhibiting, or preventing chronic rhinosinusitis in a subject comprising the step of administering to a subject a compound comprising a lipid or phospholipid moiety bond to a physiologically acceptable monomer, dimer, oligomer, or polymer, and/or a pharmaceutically acceptable salt or a pharmaceutical product thereof. This invention also provides a method of treating, suppressing, inhibiting, or preventing nasal polyps (NP) in a subject comprising the step of administering to a subject a compound comprising a lipid or phospholipid moiety bond to a physiologically acceptable monomer, dimer, oligomer, or polymer, and/or a pharmaceutically acceptable salt or a pharmaceutical product thereof.

BACKGROUND OF THE INVENTION

Lipid-conjugates having a pharmacological activity of inhibiting the enzyme phospholipase A2 (PLA2, EC 3.1.1.4) are known in the prior art. Phospholipase A2 catalyzes the breakdown of phospholipids at the sn-2 position to produce a fatty acid and a lysophospholipid. The activity of this enzyme has been correlated with various cell functions, particularly with the production of lipid mediators such as eicosanoid production (prostaglandins, thromboxanes and leukotrienes), platelet activating factor and lysophospholipids.

Glycosaminoglycans (GAG) are macro-molecules that protect the cell membrane from attacks or stimuli by a multitude of extra-cellular agents such as: Free radicals (ROS), exogenous PLA2, interleukins and other inflammatory mediators, allergens, growth factors, and degrading enzymes or invasion-promoting enzymes (e.g., heparinase, collagenase, heparanase, hyaluronidase). GAG enrichment assists in protecting cells from damage.

Since their inception, lipid-conjugates have been subjected to intensive laboratory investigation in order to obtain a wider scope of protection of cells and organisms from injurious agents and pathogenic processes.

Chronic rhinosinusitis (CRS) is a chronic inflammatory disease of the sinuses and upper airways.

CRS is now defined as a group of disorders characterized by inflammation of the mucosa of the nose and paranasal sinuses of at least 12 weeks duration. The group of CRS disorders annually accounts as many as 22 million office visits and more than 500,000 emergency department visits in the U.S., according to some estimates. Annual CRS-related healthcare expenditures may reach as much as $3.5 billion.

Clinically, CRS is a heterogenous symptom complex, often resistant to medical therapy that is typically characterized by two or more of the following: mucopurulent drainage, nasal obstruction, facial pain/pressure and hyposmia/anosmia. CRS is clinically classified into CRS with nasal polyps (CRSwNP) and CRS without nasal polyps (CRSsNP). Often, CRSwNP is associated with nasal obstruction and smell loss, and CRSsNP is associated with facial pain/pressure and headaches.

Chronic rhinosinusitis with nasal polyps is a multifactorial disease, frequently associated with asthma and occasionally with aspirin sensitivity. Chronic rhinosinusitis with nasal polyps has mainly Th2 characteristics, with Eosinophilia and a typical cytokine profile.

*Staphylococcus Aureus* Superantigens (SAS) may be involved in the amplification of the inflammation and exacerbation of the disease. *S. Aureus* is the most common microorganism isolated from mucus adjacent to massive NP (60-70% of the cases), and IgE specific to SAS is often found in NP tissue. In addition, *S. Aureus* produce enterotoxins capable of acting on peripheral blood T lymphocytes stimulating cytokine production.

SUMMARY OF THE INVENTION

In one embodiment, the invention provides for a method of treating chronic rhinosinusitis in a subject comprising the step of administering to said subject a compound represented by the structure of the general formula (A):

(A)

wherein
L is a lipid or a phospholipid;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer; and
n is a number from 1 to 1000.

In another embodiment, the invention provides a method of preventing chronic rhinosinusitis in a subject, comprising the step of administering to said subject a compound represented by the structure of the general formula (A):

(A)

wherein
L is a lipid or a phospholipid;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer; and
n is a number from 1 to 1000.

In another embodiment, the invention provides a method of treating nasal polyps in a subject, comprising the step of administering to said subject a compound represented by the structure of the general formula (A):

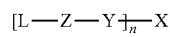

wherein
L is a lipid or a phospholipid;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer; and
n is a number from 1 to 1000.

In another embodiment, the invention provides a method of preventing nasal polyps in a subject, comprising the step of administering to said subject a compound represented by the structure of the general formula (A):

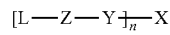

wherein
L is a lipid or a phospholipid;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer; and
n is a number from 1 to 1000.

In one embodiment, X in general formula (A) is a polysaccharide. In one embodiment, the polysaccharide is carboxymethylcellulose, while in another embodiment, the polysaccharide is a glycosaminoglycan. In one embodiment, the glycosaminoglycan is hyaluronic acid, while in another embodiment, the glycosaminoglycan is heparin. In one embodiment L in general formula (A) is phosphatidylethanolamine, which in one embodiment is dipalmitoyl phosphatidylethanolamine.

DETAILED DESCRIPTION OF THE INVENTION

Figure 1:
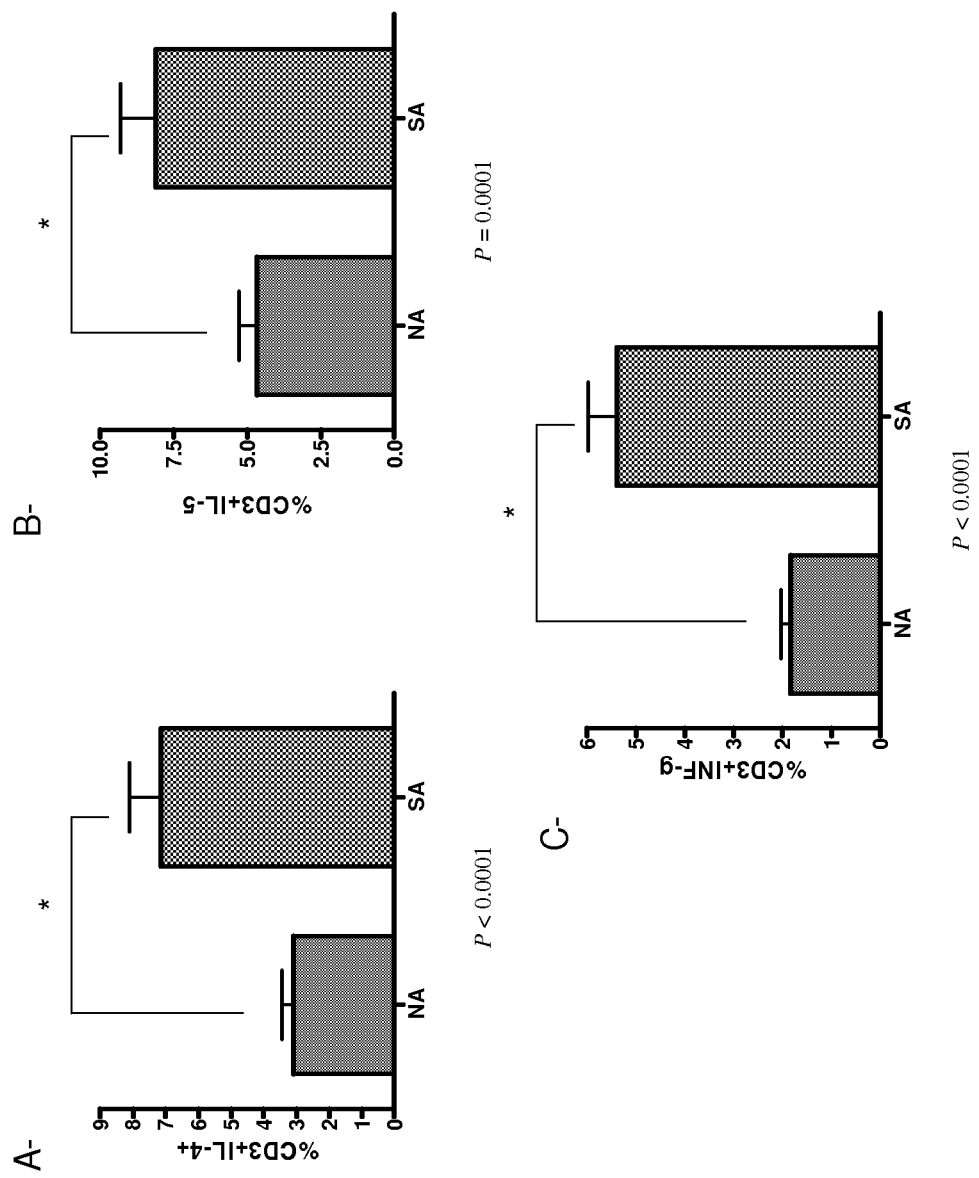
FIG. 1. Treatment of T cells from nasal polyps in vitro with *Staphylococcus Aureus* Superantigens (SA) induced the release of large amounts of IL-4, IL-5 and INF-γ compared to untreated nasal polyp T cells (NA).

The invention provides a novel method of use for lipid-conjugates which display a wide-range combination of cytoprotective pharmacological activities. These compounds can alleviate airway obstruction in asthma, protect mucosal tissue in gastrointestinal disease, suppress immune responses, alleviate cutaneous hypersensitivity reactions, inhibit cell proliferation associated with vascular injury and immunological responses, inhibit cell migration associated with vascular and central nervous system disease, attenuate oxidative damage to tissue proteins and cell membranes, interfere with viral spread, reduce tissue destroying enzyme activity, and reduce intracellular levels of chemokines and cytokines. Thus these compounds are useful in the treatment of a diversity of disease states, including asthma, rhinitis, allergic rhinitis, chronic obstructive pulmonary disease, obstructive respiratory disease, colitis, Crohn's disease, central nervous system insult, multiple sclerosis, contact dermatitis, psoriasis, cardiovascular disease, invasive medical procedures, invasive cellular proliferative disorders, anti-oxidant therapy, hemolytic syndromes, sepsis, acute respiratory distress syndrome, tissue transplant rejection syndromes, autoimmune disease, viral infection, and hypersensitivity conjunctivitis.

In one embodiment, the invention provides a method of treating an obstructive respiratory disease in a subject comprising the step of administering to said subject a compound represented by the structure of the general formula (A):

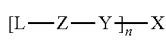

wherein
L is a lipid or a phospholipid;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer; and
n is a number from 1 to 1000.

In another embodiment, the invention provides a method of preventing an obstructive respiratory disease in a subject, comprising the step of administering to said subject a compound represented by the structure of the general formula (A):

wherein
L is a lipid or a phospholipid;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer; and
n is a number from 1 to 1000.

In another embodiment, the obstructive respiratory disease is rhinosinusitis. In another embodiment, the obstructive respiratory disease comprises a physical or anatomical obstruction, which in one embodiment, is a nasal polyp. In another embodiment, the obstructive respiratory disease is rhinitis. In another embodiment, the obstructive respiratory disease is sinusitis. In one embodiment, the obstructive respiratory disease is asthma. In another embodiment, the obstructive respiratory disease is allergic rhinitis. In another embodiment, the obstructive respiratory disease is chronic obstructive pulmonary disorder. In another embodiment, the obstructive respiratory disease is nasal polyposis.

In one embodiment, the obstructive respiratory disease is chronic. In another embodiment, the obstructive respiratory disease is acute. In another embodiment, the obstructive respiratory disease is seasonal.

In one embodiment, the invention provides a method of treating chronic rhinosinusitis in a subject comprising the step of administering to said subject a compound represented by the structure of the general formula (A):

wherein
L is a lipid or a phospholipid;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer; and
n is a number from 1 to 1000.

In another embodiment, the invention provides a method of preventing chronic rhinosinusitis in a subject, comprising the step of administering to said subject a compound represented by the structure of the general formula (A):

wherein
L is a lipid or a phospholipid;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer; and
n is a number from 1 to 1000.

In another embodiment, the invention provides a method of treating nasal polyps in a subject, comprising the step of administering to said subject a compound represented by the structure of the general formula (A):

wherein
L is a lipid or a phospholipid;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer; and
n is a number from 1 to 1000.

In another embodiment, the invention provides a method of preventing nasal polyps in a subject, comprising the step of administering to said subject a compound represented by the structure of the general formula (A):

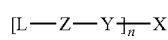

wherein
L is a lipid or a phospholipid;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer; and
n is a number from 1 to 1000.

In one embodiment, X in general formula (A) is a polysaccharide. In one embodiment, the polysaccharide is carboxymethylcellulose, while in another embodiment, the polysaccharide is a glycosaminoglycan. In one embodiment, the glycosaminoglycan is hyaluronic acid, while in another embodiment, the glycosaminoglycan is heparin. In one embodiment L in general formula (A) is phosphatidylethanolamine, which in one embodiment is dipalmitoyl phosphatidylethanolamine.

In another embodiment, the invention provides for the use of a compound represented by the structure of the general formula (A):

wherein
L is a lipid or a phospholipid;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer; and
n is a number from 1 to 1000 for the preparation of a composition to treat chronic rhinosinusitis.

In another embodiment, the invention provides for the use of a compound represented by the structure of the general formula (A):

wherein
L is a lipid or a phospholipid;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer; and
n is a number from 1 to 1000 for the preparation of a composition to prevent chronic rhinosinusitis.

In another embodiment, the invention provides for the use of a compound represented by the structure of the general formula (A):

wherein

L is a lipid or a phospholipid;

Z is either nothing, ethanolamine, serine, inositol, choline, or glycerol;

Y is either nothing or a spacer group ranging in length from 2 to 30 atoms;

X is a physiologically acceptable monomer, dimer, oligomer, or polymer; and n is a number from 1 to 1000 for the preparation of a composition to treat nasal polyps.

In another embodiment, the invention provides for the use of a compound represented by the structure of the general formula (A):

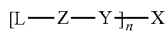
(A)

wherein

L is a lipid or a phospholipid;

Z is either nothing, ethanolamine, serine, inositol, choline, or glycerol;

Y is either nothing or a spacer group ranging in length from 2 to 30 atoms;

X is a physiologically acceptable monomer, dimer, oligomer, or polymer; and n is a number from 1 to 1000 for the preparation of a composition to prevent nasal polyps.

In another embodiment, the invention provides for the use of a compound represented by the structure of the general formula (A):

(A)

wherein

L is a lipid or a phospholipid;

Z is either nothing, ethanolamine, serine, inositol, choline, or glycerol;

Y is either nothing or a spacer group ranging in length from 2 to 30 atoms;

X is a physiologically acceptable monomer, dimer, oligomer, or polymer; and n is a number from 1 to 1000 for treating chronic rhinosinusitis.

In another embodiment, the invention provides for the use of a compound represented by the structure of the general formula (A):

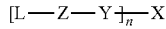
(A)

wherein

L is a lipid or a phospholipid;

Z is either nothing, ethanolamine, serine, inositol, choline, or glycerol;

Y is either nothing or a spacer group ranging in length from 2 to 30 atoms;

X is a physiologically acceptable monomer, dimer, oligomer, or polymer; and n is a number from 1 to 1000 for preventing chronic rhinosinusitis.

In another embodiment, the invention provides for the use of a compound represented by the structure of the general formula (A):

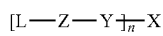
(A)

wherein

L is a lipid or a phospholipid;

Z is either nothing, ethanolamine, serine, inositol, choline, or glycerol;

Y is either nothing or a spacer group ranging in length from 2 to 30 atoms;

X is a physiologically acceptable monomer, dimer, oligomer, or polymer; and n is a number from 1 to 1000 for treating nasal polyps.

In another embodiment, the invention provides for the use of a compound represented by the structure of the general formula (A):

(A)

wherein

L is a lipid or a phospholipid;

Z is either nothing, ethanolamine, serine, inositol, choline, or glycerol;

Y is either nothing or a spacer group ranging in length from 2 to 30 atoms;

X is a physiologically acceptable monomer, dimer, oligomer, or polymer; and n is a number from 1 to 1000 for preventing nasal polyps.

In one embodiment, compositions of the present invention may be used to treat, suppress, inhibit or prevent rhinosinusitis. In one embodiment, rhinosinusitis is an inflammation of the nasal cavity and sinuses. In one embodiment, chronic rhinosinusitis (CRS) is a chronic inflammatory disease of the sinuses and upper airways.

In one embodiment, "chronic" rhinosinusitus lasts 12 weeks or more. In another embodiment, CRS lasts more than 4 weeks. In another embodiment, CRS lasts more than 6 weeks. In another embodiment, CRS lasts more than 8 weeks. In another embodiment, CRS lasts more than 10 weeks. In another embodiment, CRS lasts more than 14 weeks. In another embodiment, CRS lasts more than 16 weeks. In another embodiment, CRS lasts for months to years.

In one embodiment, CRS is initially caused by a stimulus, such as an allergen, environmental stimulus, fungus, bacteria, or virus. In one embodiment, the bacterial infection is *Staphylococcus Aureus*. In one embodiment, the fungus or bacteria colonizes the sinus in CRS thereby causing an aggressive inflammatory reaction. In another embodiment, any of the stimuli described hereinabove lead to an inflammatory reaction of CRS.

In one embodiment, compositions of the present invention may be used to treat, suppress, inhibit or prevent a polyp, which in one embodiment, is a nasal polyp. In one embodiment, a polyp is an overgrowth of tissue from the surface of a body organ. In one embodiment, a polyp may have a round, droplet, or irregular shape. In one embodiment, compositions of the present invention may be used to treat, suppress, inhibit or prevent nasal polyposis.

In another embodiment, the invention provides a method of decreasing cytokine levels in a subject, comprising the step of administering to said subject a compound of the present invention. In another embodiment, the invention provides a method of returning elevated cytokine levels to basal levels in a subject, comprising the step of administering to said subject a compound of the present invention. In another embodiment, the invention provides a method of decreasing IL-13 levels in a subject, comprising the step of administering to said subject a compound of the present invention. In another embodiment, the invention provides a method of decreasing IL-5 levels in a subject, comprising the step of administering to said subject a compound of the present invention. In another embodiment, the invention provides a method of decreasing interferon-γ levels in a subject, comprising the step of administering to said subject a compound of the present invention. In another embodiment, the invention provides a method of reversing increased IL-13 levels in a subject, comprising the step of administering to said subject a compound of the present invention. In another embodiment, the invention provides a method of reversing increased IL-5 levels in a subject, comprising the step of administering to said subject a compound of the present invention. In another embodiment, the invention provides a method of reversing increased interferon-γ levels in a subject, comprising the step of administering to said subject a compound of the present invention.

In one embodiment, X in general formula (A) is a polysaccharide. In one embodiment, the polysaccharide is carboxymethylcellulose, while in another embodiment, the polysaccharide is a glycosaminoglycan. In one embodiment, the glycosaminoglycan is hyaluronic acid, while in another embodiment, the glycosaminoglycan is heparin. In one embodiment L in general formula (A) is phosphatidylethanolamine, which in one embodiment is dipalmitoyl phosphatidylethanolamine.

In one embodiment, "treating" or "preventing" refers to delaying the onset of symptoms, reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, preventing relapse to a disease, decreasing the number or frequency of relapse episodes, increasing latency between symptomatic episodes, increasing time to sustained progression, expediting remission, inducing remission, augmenting remission, speeding recovery, or increasing efficacy of or decreasing resistance to alternative therapeutics.

In one embodiment, symptoms are primary, while in another embodiment, symptoms are secondary. In one embodiment, "primary" refers to a symptom that is a direct result of infection with a pathogen, while in one embodiment, "secondary" refers to a symptom that is derived from or consequent to a primary cause.

In one embodiment, the invention provides a method of treating a subject suffering from chronic rhinosinusitis, comprising the step of administering to a subject a compound comprising a lipid or phospholipid moiety bond to a physiologically acceptable monomer, dimer, oligomer, or polymer, and/or a pharmaceutically acceptable salt or a pharmaceutical product thereof, in an amount effective to treat the subject suffering from chronic rhinosinusitis. In another embodiment, the invention provides a method of treating a subject suffering from chronic rhinosinusitis, comprising the step of administering to a subject any one of the compounds according to the invention, in an amount effective to treat the subject suffering from an chronic rhinosinusitis. In another embodiment, the chronic rhinosinusitis is chronic rhinosinusitis with polyps.

In one embodiment, the invention provides a method of treating a subject suffering from an obstructive respiratory disease, comprising the step of administering to a subject a compound comprising a lipid or phospholipid moiety bond to a physiologically acceptable monomer, dimer, oligomer, or polymer, and/or a pharmaceutically acceptable salt or a pharmaceutical product thereof, in an amount effective to treat the subject suffering from an obstructive respiratory disease. In another embodiment, the invention provides a method of treating a subject suffering from an obstructive respiratory disease, comprising the step of administering to a subject any one of the compounds according to the invention, in an amount effective to treat the subject suffering from an obstructive respiratory disease. In another embodiment, the obstructive respiratory disease is asthma.

In one embodiment of the invention, the physiologically acceptable monomer is either a salicylate, salicylic acid, aspirin, a monosaccharide, lactobionic acid, maltose, an amino acid, glycine, carboxylic acid, acetic acid, butyric acid, dicarboxylic acid, glutaric acid, succinic acid, fatty acid, dodecanoic acid, didodecanoic acid, bile acid, cholic acid, cholesterylhemmisuccinate; or wherein the physiologically acceptable dimer or oligomer is a dipeptide, a disaccharide, a trisaccharide, an oligopeptide, or a di- or trisaccharide monomer unit of heparin, heparan sulfate, keratin, keratan sulfate, chondroitin, chondroitin sulfate, dermatin, dermatan sulfate, dextran, or hyaluronic acid; or wherein the physiologically acceptable polymer is a glycosaminoglycan, polygelin ('hemaccell'), alginate, hydroxyethyl starch (hetastarch), polyethylene glycol, polycarboxylated polyethylene glycol, chondroitin sulfate, keratin, keratin sulfate, heparan sulfate, dermatin, dermatan sulfate, carboxymethylcellulose, heparin, dextran, or hyaluronic acid. In another embodiment, the physiologically acceptable polymer is chondroitin sulfate. In another embodiment, the chondroitin sulfate is chondroitin-6-sulfate, chondroitin-4-sulfate or a derivative thereof. In another embodiment, the physiologically acceptable polymer is hyaluronic acid.

In one embodiment of the invention, the lipid or phospholipid moiety is either phosphatidic acid, an acyl glycerol, monoacylglycerol, diacylglycerol, triacylglycerol, sphingosine, sphingomyelin, chondroitin-4-sulphate, chondroitin-6-sulphate, ceramide, phosphatidylethanolamine, phosphatidylserine, phosphatidylcholine, phosphatidylinositol, or phosphatidylglycerol, or an ether or alkyl phospholipid derivative thereof, and the physiologically acceptable monomer or polymer moiety is either aspirin, lactobionic acid, maltose, glutaric acid, polyethylene glycol, carboxymethylcellulose, heparin, dextran, hemacell, hetastarch, or hyaluronic acid. In another embodiment, the phospholipid moiety is phosphatidylethanolamine.

In one embodiment, obstructive respiratory disease is a disease of luminal passages in the lungs, marked by dyspnea, tachypnea, or auscultatory or radiological signs of airway obstruction. Obstructive respiratory disease comprises asthma, acute pulmonary infections, acute respiratory distress syndrome, chronic obstructive pulmonary disease, rhinitis, and allergic rhinitis. In one embodiment, the pathophysiology is attributed to obstruction of air flow due to constriction of airway lumen smooth muscle and accumulation of infiltrates in and around the airway lumen.

In one embodiment, asthma is a disease process wherein the bronchi may be narrowed, making breathing difficult. In one embodiment, symptoms comprise wheezing, difficulty breathing (particularly exhaling air), tightness in the chest, or a combination thereof. In one embodiment, factors which can exacerbate asthma include rapid changes in temperature or humidity, allergies, upper respiratory infections, exercise, stress, smoke (e.g., cigarette), or a combination thereof.

In one embodiment, rhinitis comprises an inflammation of the mucous membrane of the nose. In one embodiment, allergic rhinitis is an inflammatory response in the nasal passages to an allergic stimulus. In one embodiment, symptoms comprise nasal congestion, sneezing, runny, itchy nose, or a combination thereof.

In one embodiment, chronic obstructive pulmonary disease is a progressive disease process that most commonly results from smoking. In one embodiment, chronic obstructive pulmonary disease comprises difficulty breathing, wheezing, coughing, which may be a chronic cough, or a combination thereof. In one embodiment, chronic obstructive pulmonary disease may lead to health complications, which in one embodiment, may comprise bronchitis, pneumonia, lung cancer, or a combination thereof.

Cellular elaboration of cytokines and chemokines serve an important regulatory function in health; however, when a hyperactive response to stress or disease is triggered, these compounds may present in excess and damage tissue, thereby pushing the disease state toward further deterioration. Cytokine overproduction is involved in numerous diseases, such as sepsis, airway and lung injury, renal failure, transplant rejection, skin injuries, intestine injuries, cancer development and metastasis, central nervous system disorders, vaginal bacterial infection, and more.

In one embodiment, the present invention offers methods for the treatment of disease based upon administration of lipids covalently conjugated through their polar head group to a physiologically acceptable chemical moiety, which may be of high or low molecular weight.

In one embodiment, the lipid compounds (Lipid-conjugates) of the present invention are described by the general formula:

[phosphatidylethanolamine-Y]$n$-X

[phosphatidylserine-Y]$n$-X

[phosphatidylcholine-Y]$n$-X

[phosphatidylinositol-Y]$n$-X

[phosphatidylglycerol-Y]$n$-X

[phosphatidic acid-Y]$n$-X

[lyso-phospholipid-Y]$n$-X

[diacyl-glycerol-Y]$n$-X

[monoacyl-glycerol-Y]$n$-X

[sphingomyelin-Y]$n$-X

[sphingosine-Y]$n$-X

[ceramide-Y]$n$-X wherein
Y is either nothing or a spacer group ranging in length from 2 to 30 atoms; and
X is a physiologically acceptable monomer, dimer, oligomer or polymer; and
n, the number of lipid molecules bound to X, is a number from 1 to 1000.

In one embodiment of this invention, n is a number from 1 to 1000. In another embodiment, n is a number from 1 to 500. In another embodiment, n is a number from 2 to 500. In another embodiment, n is a number from 2 to 1000. In another embodiment, n is a number from 1 to 100. In another embodiment, n is a number from 100 to 300. In another embodiment, n is a number from 300 to 500. In another embodiment, n is a number from 500 to 800.

In one embodiment, the lipid compounds of this invention, known herein as lipid conjugates (Lipid-conjugates) are now disclosed to possess a combination of multiple and potent pharmacological effects in addition to the ability to inhibit the extracellular form of the enzyme phospholipase A2. The set of compounds comprising phosphatidylethanolamine covalently bound to a physiologically acceptable monomer or polymer is referred to herein as the PE-conjugates. Related derivatives, in which either phosphatidylserine, phosphatidylcholine, phosphatidylinositol, phosphatidic acid or phosphatidylglycerol are employed in lieu of phosphatidylethanolamine as the lipid moiety provide equivalent therapeutic results, based upon the biological experiments described below for the Lipid-conjugates and the structural similarities shared by these compounds. Other Lipid-conjugate derivatives relevant to this invention are Lipid-conjugates wherein at least one of the fatty acid groups of the lipid moieties at position C1 or C2 of the glycerol backbone are substituted by a long chain alkyl group attached in either ether or alkyl bonds, rather than ester linkage.

As defined by the structural formulae provided herein for the Lipid-conjugates, these compounds may contain between one to one thousand lipid moieties bound to a single physiologically acceptable polymer molecule.

Administration of the Lipid-conjugates in a diversity of animal and cell models of disease invokes remarkable, and unexpected, cytoprotective effects, which are useful in the treatment of disease. They are able to stabilize biological membranes; inhibit cell proliferation; suppress free radical production; suppress nitric oxide production; reduce cell migration across biological barriers; influence chemokine levels, including MCP-1, ENA-78, Gro α, and CX3C; affect gene transcription and modify the expression of MHC antigens; bind directly to cell membranes and change the water structure at the cell surface; inhibit the uptake of oxidized lipoprotein; prevent airway smooth muscle constriction; suppress neurotransmitter release; reduce expression of tumor necrosis factor-α (TNF-α); modify expression of transcription factors such as NFκB; inhibit extracellular degradative enzymes, including collagenase, heparinase, hyaluronidase, in addition to that of PLA2; and inhibit viral infection of white cells. Thus the Lipid-conjugates provide far-reaching cytoprotective effects to an organism suffering from a disease wherein one or more of the presiding pathophysiological mechanisms of tissue damage entails either oxidation insult giving rise to membrane fragility; hyperproliferation behavior of cells giving rise to stenotic plaque formation in vascular tissue, angiogenesis and benign or malignant cancer disease, or psoriasis; aberrant cell migration giving rise to brain injury or tumor cell metastases; excessive expression of chemokines and cytokines associated with central nervous system (CNS) insult, sepsis, ARDS, or immunological disease; cell membrane damage giving rise to CNS insult, CVS disease, or hemolysis; peroxidation of blood proteins and cell membranes giving rise to atherosclerosis or reperfusion injury; excessive nitric oxide production giving rise to CNS insult, reperfusion injury, and septic shock; interaction with major histocompatability antigens (MHC) associated with autoimmune diseases and alloimmune syndromes, such as transplant rejection.

In one embodiment of the present invention, the useful pharmacological properties of the lipid or Lipid-conjugates may be applied for clinical use, and disclosed herein as methods for treatment of a disease. The biological basis of these methods may be readily demonstrated by standard cellular and animal models of disease as described below.

While pharmacological activity of the Lipid-conjugates described herein may be due in part to the nature of the lipid moiety, the multiple and diverse combination of pharmacological properties observed for the Lipid-conjugates emerges from the ability of the compound structure to act essentially as several different drugs in one chemical entity. Thus, for example, internal mucosal injury, as may occur in colitis or Crohn's disease, may be attenuated by any one or all of the pharmaceutical activities of immune suppression, anti-inflammation, anti-oxidation, nitric oxide production, or membrane stabilization. Protection of blood vessels from periluminal damage, as may occur in atherosclerosis, may entail activity from anti-proliferative, anti-chemokine, antioxidant, or antimigratory effects. Treatment or prevention of chronic rhinosinusitis, nasal polyps, or obstructive respiratory disease may involve any one of the many activities of the Lipid-conjugates ranging from suppression of nitric oxide, anti-chemokine, anti-proliferative, or membrane stabilization effects.

The use of a single chemical entity with potent anti-oxidant, membrane-stabilizing, anti-proliferative, anti-chemokine, anti-migratory, and anti-inflammatory activity provides increased cytoprotection relative to the use of several different agents each with a singular activity. The use of a single agent having multiple activities over a combination or plurality of different agents provides uniform delivery of an active molecule, thereby simplifying issues of drug metabolism, toxicity and delivery. The compounds of the present invention also exhibit properties present only in the combined molecule, not in the individual components.

In one embodiment, the compounds of the invention may be used for acute treatment of temporary conditions, or may be administered chronically, especially in the case of progressive, recurrent, or degenerative disease. In one embodiment of the invention, the concentrations of the compounds will depend on various factors, including the nature of the condition to be treated, the condition of the patient, the route of administration and the individual tolerability of the compositions.

In another embodiment, the invention provides low-molecular weight Lipid-conjugates, previously undisclosed and unknown to possess pharmacological activity, of the general formula:

[Phosphatidylethanolamine-Y]$_n$–X

[Phosphatidylserine-Y]$_n$–X

[Phosphatidylcholine-Y]$_n$–X

[Phosphatidylinositol-Y]$_n$–X

[Phosphatidylglycerol-Y]$_n$–X

[Phosphatidic acid-Y]$_n$–X

[lyso-phospholipid-Y]$_n$–X

[diacyl-glycerol-Y]$_n$–X

[monoacyl-glycerol-Y]$_n$–X

[sphingomyelin-Y]$_n$–X

[sphingosine-Y]$_n$–X

[ceramide-Y]$_n$–X wherein

Y is either nothing or a spacer group ranging in length from 2 to 30 atoms; and

X is salicylate, salicylic acid, aspirin, a monosaccharide, lactobionic acid, maltose, an amino acid, glycine, carboxylic acid, acetic acid, butyric acid, dicarboxylic acid, glutaric acid, succinic acid, fatty acid, dodecanoic acid, didodecanoic acid, bile acid, cholic acid, cholesterylhemmisuccinate, a dipeptide, a disaccharide, a trisaccharide, an oligosaccharide, an oligopeptide, or a di- or trisaccharide monomer unit of heparin, heparan sulfate, keratin, keratan sulfate, chondroitin, chondroitin-6-sulfate, chondroitin-4-sulfate, dermatin, dermatan sulfate, dextran, or hyaluronic acid, a glycosaminoglycan, polygeline ('haemaccel'), alginate, hydroxyethyl starch (hetastarch), polyethylene glycol, polycarboxylated polyethylene glycol, chondroitin-6-sulfate, chondroitin-4-sulfate, keratin, keratin sulfate, heparan sulfate, dermatin, dermatan sulfate, carboxymethylcellulose, heparin, dextran, or hyaluronic acid; and n, the number of lipid molecules bound to X, is a number from 1 to 1000.

In one embodiment of this invention, n is a number from 1 to 1000. In another embodiment, n is a number from 1 to 500. In another embodiment, n is a number from 1 to 100. In another embodiment, n is a number from 100 to 300. In another embodiment, n is a number from 300 to 500. In another embodiment, n is a number from 500 to 800.

In another embodiment of the invention, these Lipid-conjugate derivatives possess wide-spectrum pharmacological activity and, as pharmaceutical agents administered to treat disease, are considered analogous to the Lipid-conjugates comprised from high molecular weight polymers. Other lipid-conjugate derivatives relevant to this invention are glycerolipid moieties in which at least one of the two long chain alkyl groups in position C1 and C2 of the glycerol backbone are attached in ether or alkyl bonds, rather than ester linkage.

The present invention is further illustrated in the following examples of the therapeutic Lipid-conjugate compounds, their chemical preparation, their anti-disease activity, and methods of use as pharmaceutical compositions in the treatment of disease.

Compounds

In the methods, according to embodiments of the invention, the Lipid-conjugates administered to the subject are comprised from at least one lipid moiety covalently bound through an atom of the polar head group to a monomer or polymeric moiety (referred to herein as the conjugated moiety) of either low or high molecular weight. When desired, an optional bridging moiety can be used to link the Lipid-conjugates moiety to the monomer or polymeric moiety. The conjugated moiety may be a low molecular weight carboxylic acid, dicarboxylic acid, fatty acid, dicarboxylic fatty acid, acetyl salicylic acid, cholic acid, cholesterylhemisuccinate, or mono- or di-saccharide, an amino acid or dipeptide, an oligopeptide, a glycoprotein mixture, a di- or trisaccharide monomer unit of a glycosaminoglycan such as a repeating unit of heparin, heparan sulfate, hyaluronic acid, chondroitin-sulfate, dermatan, keratan sulfate, or a higher molecular weight peptide or oligopeptide, a polysaccharide, polyglycan, protein, glycosaminoglycan, or a glycoprotein mixture. From a composition aspect, phospholipid-conjugates of high molecular weight, and associated analogues, are the subject of U.S. Pat. No. 5,064,817, as well as the publications cited herein.

In one embodiment of the invention, when the conjugated carrier moiety is a polymer, the ratio of lipid moieties covalently bound may range from one to one thousand lipid residues per polymer molecule, depending upon the nature of the polymer and the reaction conditions employed. For example, the relative quantities of the starting materials, or the extent of the reaction time, may be modified in order to obtain Lipid-conjugate products with either high or low ratios of lipid residues per polymer, as desired.

The term "moiety" means a chemical entity otherwise corresponding to a chemical compound, which has a valence satisfied by a covalent bond.

Examples of polymers which can be employed as the conjugated moiety for producing Lipid-conjugates for use in the methods of this invention may be physiologically acceptable polymers, including water-dispersible or -soluble polymers of various molecular weights and diverse chemical types, mainly natural and synthetic polymers, such as glycosaminoglycans, hyaluronic acid, heparin, heparin sulfate, chondroitin sulfate, chondroitin-6-sulfate, chondroitin-4-sulfate, keratin sulfate, dermatin, sulfate, plasma expanders, including polygeline ("Haemaccel", degraded gelatin polypeptide crosslinked via urea bridges, produced by "Behring"), "hydroxyethylstarch" (Htastarch, HES) and extrans, food and drug additives, soluble cellulose derivatives (e.g., methylcellulose, carboxymethylcellulose), polyaminoacids, hydrocarbon polymers (e.g., polyethylene), polystyrenes, polyesters, polyamides, polyethylene oxides (e.g., polyethyleneglycols, polycarboxyethyleneglycol), polyvinnylpyrrolidones, polysaccharides, alginates, assimilable gums (e.g., xanthan gum), peptides, injectable blood proteins (e.g., serum albumin), cyclodextrin, and derivatives thereof.

Examples of monomers, dimers, and oligomers which can be employed as the conjugated moiety for producing Lipid-conjugates for use in the methods of the invention may be mono- or disaccharides, carboxylic acid, dicarboxylic acid, fatty acid, dicarboxylic fatty acid, acetyl salicylic acid, cholic acid, cholesterylhemisuccinate, and di- and trisaccharide unit monomers of glycosaminoglycans including heparin, heparan sulfate, hyaluronic acid, chondroitin, chondroitin-6-sulfate, chondroitin-4-sulfate, dermatin, dermatan sulfate, keratin, keratan sulfate, or dextran.

In some cases, according to embodiments of the invention, the monomer or polymer chosen for preparation of the Lipid-conjugate may in itself have select biological properties. For example, both heparin and hyaluronic acid are materials with known physiological functions. In the present invention, however, the Lipid-conjugates formed from these substances as starting materials display a new and wider set of pharmaceutical activities than would be predicted from administration of either heparin or hyaluronic acid which have not been bound by covalent linkage to a phospholipid. It can be shown, by standard comparative experiments as described below, that phosphatidylethanolamine (PE) linked to carboxymethylcellulose (referred to as CMPE, CMC-Peor CME), to hyaluronic acid (referred to as HYPE, HyPE, and Hyal-PE), to heparin (referred to as HEPPE, HepPE, HePPE, Hepa-PE), to chondroitine sulfate A (referred to as CSAPE, CsaPE, CSAPE), to Polygeline (haemaccel) (referred to as HemPE, HEMPE), or to hydroxyethylstarch (referred to as HesPE, HESPE), are far superior in terms of potency and range of useful pharmaceutical activity to the free conjugates (the polymers above and the like). In fact, these latter substances are, in general, not considered useful in methods for treatment of most of the diseases described herein, and for those particular cases wherein their use is medically prescribed, such as ischemic vascular disease, the concentrations for their use as drugs are several orders of magnitude higher. Thus, the combination of a phospholipid such as phosphatidylethanolamine, or related phospholipids which differ with regard to the polar head group, such as phosphatidylserine (PS), phosphatidylcholine (PC), phosphatidylinositol (PI), and phosphatidylglycerol (PG), results in the formation of a compound which has novel pharmacological properties when compared to the starting materials alone.

The biologically active lipid conjugates described herein can have a wide range of molecular weight, e.g., above 50,000 (up to a few hundred thousands) when it is desirable to retain the Lipid conjugate in the vascular system and below 50,000 when targeting to extravascular systems is desirable. The sole limitation on the molecular weight and the chemical structure of the conjugated moiety is that it does not result in a Lipid-conjugate devoid of the desired biological activity, or lead to chemical or physiological instability to the extent that the Lipid-conjugate is rendered useless as a drug in the method of use described herein.

In one embodiment, the compound according to the invention is represented by the structure of the general formula (A):

(A)

wherein

L is a lipid or a phospholipid;

Z is either nothing, ethanolamine, serine, inositol, choline, or glycerol;

Y is either nothing or a spacer group ranging in length from 2 to 30 atoms;

X is a physiologically acceptable monomer, dimer, oligomer, or polymer, wherein X is a glycosaminoglycan; and n is a number from 1 to 1000;

wherein any bond between L, Z, Y and X is either an amide or an esteric bond.

In another embodiment, the compound according to the invention is represented by the structure of the general formula (I):

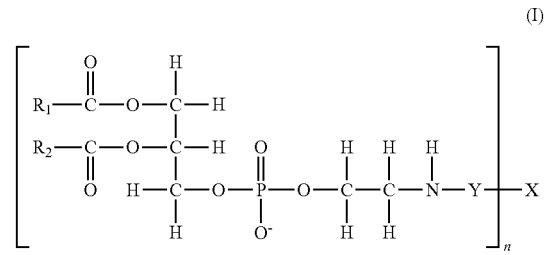

(I)

wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Y is either nothing or a spacer group ranging in length from 2 to 30 atoms; and

X is either a physiologically acceptable monomer, dimer, oligomer or a physiologically acceptable polymer, wherein X is a glycosaminoglycan; and n is a number from 1 to 1,000;

wherein if Y is nothing the phosphatidylethanolamine is directly linked to X via an amide bond and if Y is a spacer, the spacer is directly linked to X via an amide or an esteric bond and to the phosphatidylethanolamine via an amide bond.

Preferred compounds for use in the methods of the invention comprise one of the following as the conjugated moiety X: acetate, butyrate, glutarate, succinate, dodecanoate, didodecanoate, maltose, lactobionic acid, dextran, alginate, aspirin, cholate, cholesterylhemisuccinate, carboxymethylcellulose, heparin, hyaluronic acid, polygeline (haemaccel), polyethyleneglycol, and polycarboxylated polyethylene glycol. The polymers used as starting material to prepare the PE-conjugates may vary in molecular weight from 1 to 2,000 kDa.

Examples of phosphatidylethanolamine (PE) moieties are analogues of the phospholipid in which the chain length of the two fatty acid groups attached to the glycerol backbone of the phospholipid varies from 2-30 carbon atoms length, and in which these fatty acids chains contain saturated and/or unsaturated carbon atoms. In lieu of fatty acid chains, alkyl chains attached directly or via an ether linkage to the glycerol backbone of the phospholipid are included as analogues of PE. According to the present invention, a most preferred PE moiety is dipalmitoylphosphatidy-ethanolamine.

Phosphatidyl-ethanolamine and its analogues may be from various sources, including natural, synthetic, and semisynthetic derivatives and their isomers.

Phospholipids which can be employed in lieu of the PE moiety are N-methyl-PE derivatives and their analogues, linked through the amino group of the N-methyl-PE by a covalent bond; N,N-dimethyl-PE derivatives and their analogues linked through the amino group of the N,N-dimethyl-PE by a covalent bond, phosphatidylserine (PS) and its analogues, such as palmitoyl-stearoyl-PS, natural PS from various sources, semisynthetic PSs, synthetic, natural and artifactual PSs and their isomers. Other phospholipids useful as conjugated moieties in this invention are phosphatidylcholine (PC), phosphatidylinositol (PI), phosphatidic acid and phosphoatidylglycerol (PG), as well as derivatives thereof comprising either phospholipids, lysophospholipids, phosphatidyic acid, sphingomyelins, lysosphingomyelins, ceramide, and sphingosine.

For PE-conjugates and PS-conjugates, the phospholipid is linked to the conjugated monomer or polymer moiety through the nitrogen atom of the phospholipid polar head group, either directly or via a spacer group. For PC, PI, and PG conjugates, the phospholipid is linked to the conjugated monomer or polymer moiety through either the nitrogen or one of the oxygen atoms of the polar head group, either directly or via a spacer group.

In another embodiment, the compound according to the invention is represented by the structure of the general formula (II):

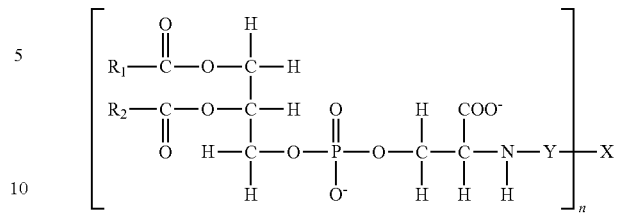

wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Y is either nothing or a spacer group ranging in length from 2 to 30 atoms;

X is a physiologically acceptable monomer, dimer, oligomer or polymer wherein x is a glycosaminoglycan; and n is a number from 1 to 1000;

wherein if Y is nothing the phosphatidylserine is directly linked to X via an amide bond and if Y is a spacer, the spacer is directly linked to X via an amide or an esteric bond and to the phosphatidylserine via an amide bond.

In another embodiment, the compound according to the invention be [phosphatidylserine-Y]n–X, wherein Y is either nothing or a spacer group ranging in length from 2 to 30 atoms, X is a physiologically acceptable monomer, dimer, oligomer or polymer wherein x is a glycosaminoglycan, and n is a number from 1 to 1000, wherein the phosphatidylserine may be bonded to Y or to X, if Y is nothing, via the COO⁻ moiety of the phosphatidylserine.

In another embodiment, the compound according to the invention is represented by the structure of the general formula (III):

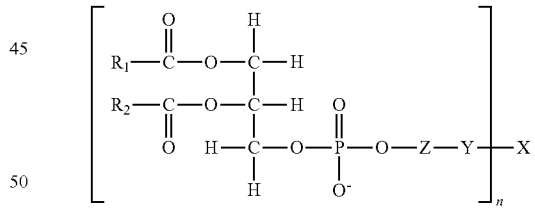

wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, inositol, choline, or glycerol;

Y is either nothing or a spacer group ranging in length from 2 to 30 atoms;

X is a physiologically acceptable monomer, dimer, oligomer, or polymer, wherein x is a glycosaminoglycan; and n is a number from 1 to 1000;

wherein any bond between the phosphatidyl, Z, Y and X is either an amide or anesteric bond.

In another embodiment, the compound according to the invention is represented by the structure of the general formula (IV)

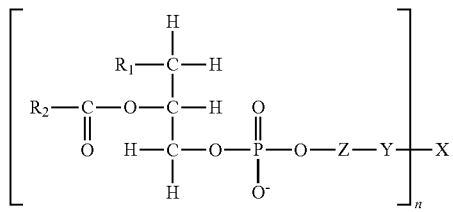

(IV)

wherein $R_1$ is either hydrogen or a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, inositol, choline, or glycerol;

Y is either nothing or a spacer group ranging in length from 2 to 30 atoms;

X is a physiologically acceptable monomer, dimer, oligomer, or polymer, wherein x is a glycosaminoglycan; and n is a number from 1 to 1000;

wherein any bond between the phospholipid, Z, Y and X is either an amide or an esteric bond.

In another embodiment, the compound according to the invention is represented by the structure of the general formula (V):

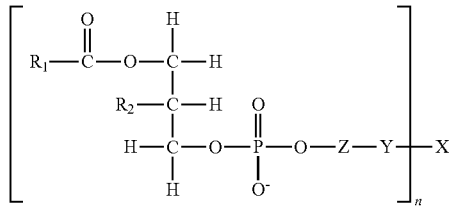

(V)

wherein $R_1$ is a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, inositol, choline, or glycerol;

Y is either nothing or a spacer group ranging in length from 2 to 30 atoms;

X is a physiologically acceptable monomer, dimer, oligomer, or polymer, wherein x is a glycosaminoglycan; and n is a number from 1 to 1000;

wherein any bond between the phospholipid, Z, Y and X is either an amide or an esteric bond.

In another embodiment, the compound according to the invention is represented by the structure of the general formula (VI):

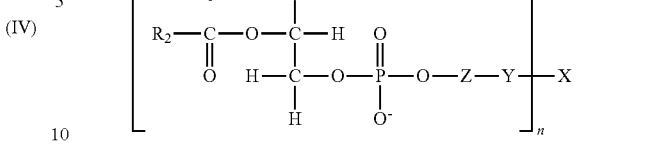

(VI)

wherein $R_1$ is either hydrogen or a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, inositol, choline, or glycerol;

Y is either nothing or a spacer group ranging in length from 2 to 30 atoms;

X is a physiologically acceptable monomer, dimer, oligomer, or polymer, wherein x is a glycosaminoglycan; and n is a number from 1 to 1000;

wherein any bond between the phospholipid, Z, Y and X is either an amide or an esteric bond.

In another embodiment, the compound according to the invention is represented by the structure of the general formula (VII):

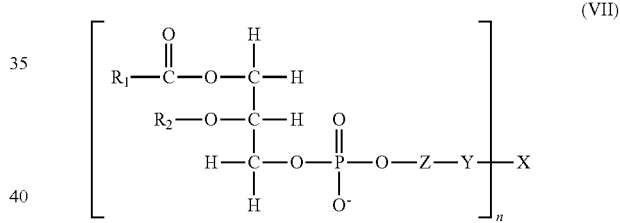

(VII)

wherein $R_1$ is a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, inositol, choline, or glycerol;

Y is either nothing or a spacer group ranging in length from 2 to 30 atoms;

X is a physiologically acceptable monomer, dimer, oligomer, or polymer, wherein x is a glycosaminoglycan; and n is a number from 1 to 1000;

wherein any bond between the phospholipid, Z, Y and X is either an amide or an esteric bond.

In one embodiment of the invention, phosphatidylcholine (PC), Phosphatidylinositol (PI), phosphatidic acid (PA), wherein Z is nothing, and Phosphatidylglycerol (PG) conjugates are herein defined as compounds of the general formula (III).

In one embodiment of the invention Y is nothing. Non limiting examples of suitable divalent groups forming the optional bridging group (spacer) Y, according to embodiments of the invention, are straight or branched chain alkylene, e.g., of 2 or more, preferably 4 to 30 carbon atoms, —CO-alkylene-CO, —NH-alkylene-NH—, —CO-alkylene-NH—, —NH-alkylene-NHCO-alkylene-NH—, an amino acid, cycloalkylene, wherein alkylene in each instance, is straight or branched chain and contains 2 or more, preferably 2 to 30 atoms in the chain, —(—O—CH(CH$_3$)CH$_2$—)$_x$— wherein x is an integer of 1 or more.

According to embodiments of the invention, in addition to the traditional phospholipid structure, related derivatives for use in this invention are phospholipids modified at the C1 or C2 position to contain an ether or alkyl bond instead of an ester bond. In one embodiment of the invention, the alkyl phospholipid derivatives and ether phospholipid derivatives are exemplified herein.

In another embodiment, the compound according to the invention is represented by the structure of the general formula (VIII):

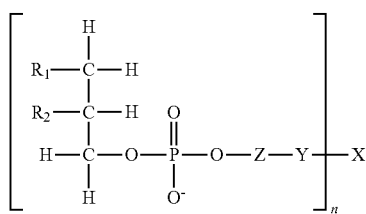

(VIII)

wherein
$R_1$ is a linear, saturated, mono-unsaturated, or poly-unsaturated, alkyl chain ranging in length from 2 to 30 carbon atoms;
$R_2$ is either hydrogen or a linear, saturated, mono-unsaturated, or poly-unsaturated, alkyl chain ranging in length from 2 to 30 carbon atoms;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer, wherein x is a glycosaminoglycan; and
n is a number from 1 to 1000;
wherein any bond between the phospholipid, Z, Y and X is either an amide or an esteric bond.

In another embodiment, the compound according to the invention is represented by the structure of the general formula (IX):

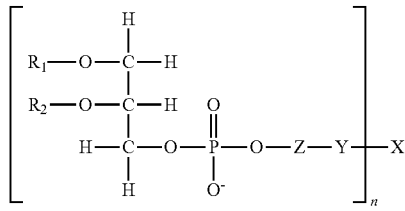

(IX)

wherein
$R_1$ is either hydrogen or a linear, saturated, mono-unsaturated, or poly-unsaturated, alkyl chain ranging in length from 2 to 30 carbon atoms;
$R_2$ is either hydrogen or a linear, saturated, mono-unsaturated, or poly-unsaturated, alkyl chain ranging in length from 2 to 30 carbon atoms;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer, wherein x is a glycosaminoglycan; and
n is a number from 1 to 1000;
wherein any bond between the phospholipid, Z, Y and X is either an amide or an esteric bond.

In another embodiment, the compound according to the invention is represented by the structure of the general formula (IXa):

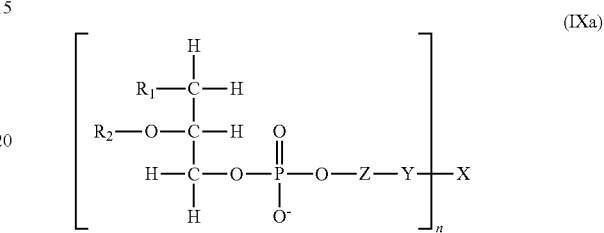

(IXa)

wherein
$R_1$ is either hydrogen or a linear, saturated, mono-unsaturated, or poly-unsaturated, alkyl chain ranging in length from 2 to 30 carbon atoms;
$R_2$ is either hydrogen or a linear, saturated, mono-unsaturated, or poly-unsaturated, alkyl chain ranging in length from 2 to 30 carbon atoms;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer, wherein x is a glycosaminoglycan; and
n is a number from 1 to 1000;
wherein any bond between the phospholipid, Z, Y and X is either an amide or an esteric bond.

In another embodiment, the compound according to the invention is represented by the structure of the general formula (IXb):

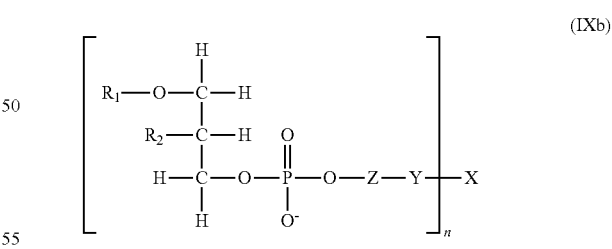

(IXb)

wherein
$R_1$ is either hydrogen or a linear, saturated, mono-unsaturated, or poly-unsaturated, alkyl chain ranging in length from 2 to 30 carbon atoms;
$R_2$ is either hydrogen or a linear, saturated, mono-unsaturated, or poly-unsaturated, alkyl chain ranging in length from 2 to 30 carbon atoms;
Z is either nothing, ethanolamine, serine, inositol, choline, or glycerol;
Y is either nothing or a spacer group ranging in length from 2 to 30 atoms;

X is a physiologically acceptable monomer, dimer, oligomer, or polymer, wherein x is a glycosaminoglycan; and n is a number from 1 to 1000;

wherein any bond between the phospholipid, Z, Y and X is either an amide or an esteric bond.

In another embodiment, the compound according to the invention is represented by the structure of the general formula (X):

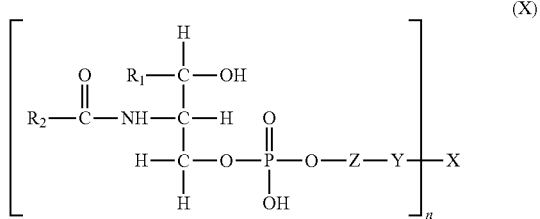

(X)

wherein $R_1$ is either hydrogen or a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, ethanolamine, serine, inositol, choline, or glycerol;

Y is either nothing or a spacer group ranging in length from 2 to 30 atoms;

X is a physiologically acceptable monomer, dimer, oligomer, or polymer, wherein x is a glycosaminoglycan; and n is a number from 1 to 1000;

wherein any bond between the ceramide phosphoryl, Z, Y and X is either an amide or an esteric bond.

In another embodiment, the compound according to the invention is represented by the structure of the general formula (XI):

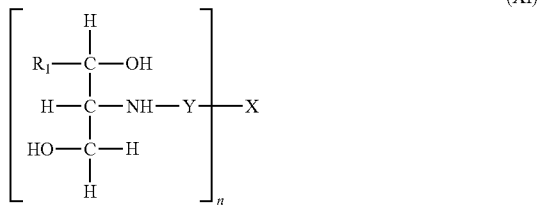

(XI)

wherein $R_1$ is a linear, saturated, mono-unsaturated, or poly-unsaturated, alkyl chain ranging in length from 2 to 30 carbon atoms;

Y is either nothing or a spacer group ranging in length from 2 to 30 atoms;

X is a physiologically acceptable monomer, dimer, oligomer or polymer, wherein x is a glycosaminoglycan; and n is a number from 1 to 1000;

wherein if Y is nothing the sphingosyl is directly linked to X via an amide bond and if Y is a spacer, the spacer is directly linked to X and to the sphingosyl via an amide bond and to X via an amide or an esteric bond.

In another embodiment, the compound according to the invention is represented by the structure of the general formula (XII):

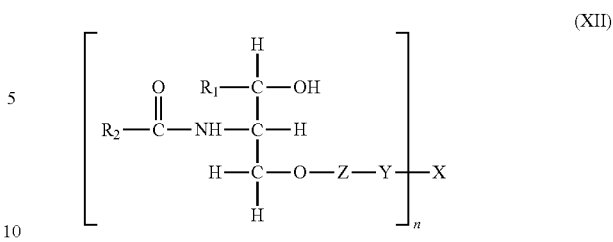

(XII)

wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

L is ceramide;

Z is either nothing, ethanolamine, serine, inositol, choline, or glycerol;

Y is either nothing or a spacer group ranging in length from 2 to 30 atoms;

X is a physiologically acceptable monomer, dimer, oligomer or polymer, wherein x is a glycosaminoglycan; and n is a number from 1 to 1000;

wherein any bond between the ceramide, Z, Y and X is either an amide or an esteric bond.

In another embodiment, the compound according to the invention is represented by the structure of the general formula (XIII):

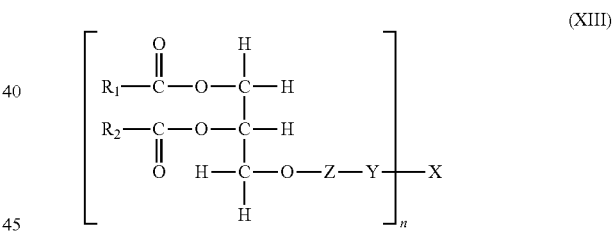

(XIII)

wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a physiologically acceptable monomer, dimer, oligomer or polymer, wherein x is a glycosaminoglycan; and n is a number from 1 to 1000;

wherein any bond between the diglyceryl, Z, Y and X is either an amide or an esteric bond.

In another embodiment, the compound according to the invention is represented by the structure of the general formula (XIV):

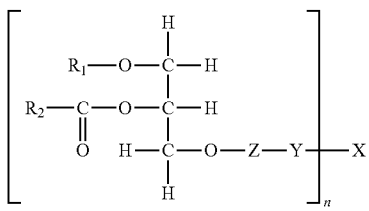

(XIV)

wherein $R_1$ is either hydrogen or a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a physiologically acceptable monomer, dimer, oligomer or polymer, wherein x is a glycosaminoglycan; and n is a number from 1 to 1000;

wherein any bond between the glycerolipid, Z, Y and X is either an amide or an esteric bond.

In another embodiment, the compound according to the invention is represented by the structure of the general formula (XV):

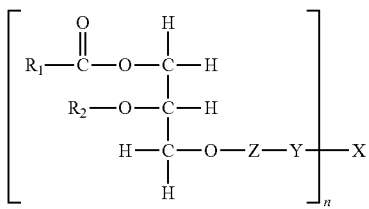

(XV)

wherein $R_1$ is a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a physiologically acceptable monomer, dimer, oligomer or polymer, wherein x is a glycosaminoglycan; and n is a number from 1 to 1000;

wherein any bond between the glycerolipid, Z, Y and X is either an amide or an esteric bond.

In another embodiment, the compound according to the invention is represented by the structure of the general formula (XVI):

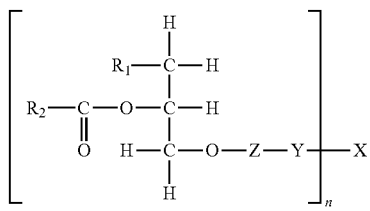

(XVI)

wherein $R_1$ is either hydrogen or a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a physiologically acceptable monomer, dimer, oligomer or polymer, wherein x is a glycosaminoglycan; and n is a number from 1 to 1000;

wherein any bond between the lipid, Z, Y and X is either an amide or an esteric bond.

In another embodiment, the compound according to the invention is represented by the structure of the general formula (XVII):

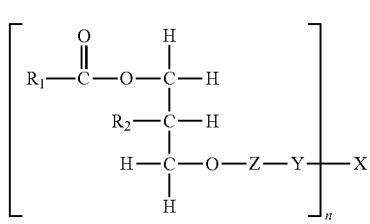

(XVII)

wherein $R_1$ is either hydrogen or a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a physiologically acceptable monomer, dimer, oligomer or polymer, wherein x is a glycosaminoglycan; and n is a number from 1 to 1000;

wherein any bond between the lipid, Z, Y and X is either an amide or an esteric bond.

In another embodiment, the compound according to the invention is represented by the structure of the general formula (XVIII):

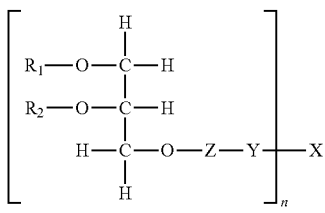

(XVIII)

wherein $R_1$ is either hydrogen or a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a physiologically acceptable monomer, dimer, oligomer or polymer, wherein x is a glycosaminoglycan; and n is a number from 1 to 1000;

wherein any bond between the lipid, Z, Y and X is either an amide or an esteric bond.

In another embodiment, the compound according to the invention is represented by the structure of the general formula (XIX):

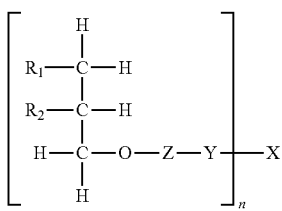

(XIX)

wherein $R_1$ is either hydrogen or a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a physiologically acceptable monomer, dimer, oligomer or polymer, wherein x is a glycosaminoglycan; and n is a number from 1 to 1000;

wherein any bond between the lipid, Z, Y and X is either an amide or an esteric bond.

In another embodiment, the compound according to the invention is represented by the structure of the general formula (XX):

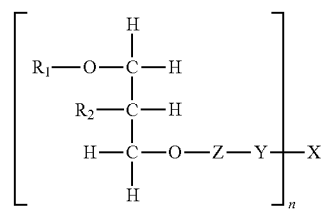

(XX)

wherein $R_1$ is either hydrogen or a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a physiologically acceptable monomer, dimer, oligomer or polymer, wherein x is a glycosaminoglycan; and n is a number from 1 to 1000;

wherein any bond between the lipid, Z, Y and X is either an amide or an esteric bond.

In another embodiment, the compound according to the invention is represented by the structure of the general formula (XXI):

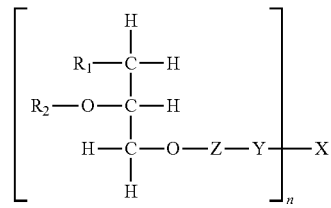

(XXI)

wherein $R_1$ is either hydrogen or a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a physiologically acceptable monomer, dimer, oligomer or polymer, wherein x is a glycosaminoglycan; and n is a number from 1 to 1000;

wherein any bond between the lipid, Z, Y and X is either an amide or an esteric bond.

In one embodiment of the invention, the glycosaminoglycan may be, inter alia, hyaluronic acid, heparin, heparan sulfate, chondroitin sulfate, keratin, keratan sulfate, dermatan sulfate or a derivative thereof.

In another embodiment, the glycosaminoglycan is di- and trisaccharide unit monomers of glycosaminoglycans. In another embodiment, the chondroitin sulfate may be, inter alia, chondroitin-6-sulfate, chondroitin-4-sulfate or a derivative thereof.

In one embodiment of the invention, the sugar rings of the glycosaminoglycan are intact. In another embodiment, intact refers to closed. In another embodiment, intact refers to natural. In another embodiment, intact refers to unbroken.

In one embodiment of the invention, the structure of the lipid or phospholipids in any compound according to the invention is intact. In another embodiment, the natural structure of the lipid or phospholipids in any compound according to the invention is maintained.

In one embodiment, the compounds according to the invention are biodegradable.

In one embodiment, the compound according to the invention is a compound represented by the structure of the general formula (A):

  (A)

wherein
L is phosphatidyl;
Z is ethanolamine, wherein L and Z are chemically bonded resulting in phosphatidylethanolamine;
Y is nothing;
X is hyaluronic acid; and
n is a number from 1 to 1000;
wherein any bond between the phosphatidylethanolamine and the hyaluronic acid is an amide bond.

In one embodiment, the compound according to the invention is a compound represented by the structure of the general formula (A):

  (A)

wherein
L is phosphatidyl;
Z is ethanolamine, wherein L and Z are chemically bonded resulting in phosphatidylethanolamine;
Y is nothing;
X is chondroitin sulfate; and
n is a number from 1 to 1000;
wherein any bond between the phosphatidylethanolamine and the chondroitin sulfate is an amide bond.

In another embodiment, the invention provides a method of treating a subject suffering from asthma, comprising the step of administering to a subject any one of the compounds according to the invention, or any combination thereof, in an amount effective to treat the subject suffering from asthma. In another embodiment, the compounds according to the invention include, inter alia, the compounds represented by the structures of the general formulae: (A), (I), (II), (III), (IV), (V), (VI), (VII), (VIII), (IX), (IXa), (IXb), (X), (XI), (XII), (XIII), (XIV), (XV), (XVI), (XVII), (XVIII), (XIX), (XX), (XXI), (XXII) or any combination thereof. In another embodiment, the invention provides a method of preventing asthma in a subject.

In another embodiment, the invention provides a method of treating a subject suffering from rhinitis, comprising the step of administering to a subject any one of the compounds according to the invention, or any combination thereof, in an amount effective to treat the subject suffering from rhinitis. In another embodiment, the compounds according to the invention include, inter alia, the compounds represented by the structures of the general formulae: (A), (I), (II), (III), (IV), (V), (VI), (VII), (VIII), (IX), (IXa), (IXb), (X), (XI), (XII), (XIII), (XIV), (XV), (XVI), (XVII), (XVIII), (XIX), (XX), (XXI), (XXII) or any combination thereof. In another embodiment, the invention provides a method of preventing rhinitis in a subject.

In another embodiment, the invention provides a method of treating a subject suffering from allergic rhinitis, comprising the step of administering to a subject any one of the compounds according to the invention, or any combination thereof, in an amount effective to treat the subject suffering from allergic rhinitis. In another embodiment, the compounds according to the invention include, inter alia, the compounds represented by the structures of the general formulae: (A), (I), (II), (III), (IV), (V), (VI), (VII), (VIII), (IX), (IXa), (IXb), (X), (XI), (XII), (XIII), (XIV), (XV), (XVI), (XVII), (XVIII), (XIX), (XX), (XXI), (XXII) or any combination thereof. In another embodiment, the invention provides a method of preventing allergic rhinitis in a subject.

In another embodiment, the invention provides a method of treating a subject suffering from chronic obstructive pulmonary disease, comprising the step of administering to a subject any one of the compounds according to the invention, or any combination thereof, in an amount effective to treat the subject suffering from chronic obstructive pulmonary disease. In another embodiment, the compounds according to the invention include, inter alia, the compounds represented by the structures of the general formulae: (A), (I), (II), (III), (IV), (V), (VI), (VII), (VIII), (IX), (IXa), (IXb), (X), (XI), (XII), (XIII), (XIV), (XV), (XVI), (XVII), (XVIII), (XIX), (XX), (XXI), (XXII) or any combination thereof. In another embodiment, the invention provides a method of preventing chronic obstructive pulmonary disease in a subject.

In another embodiment, the invention provides a method of treating a subject suffering from an obstructive respiratory disease, comprising the step of administering to a subject any one of the compounds according to the invention, or any combination thereof, in an amount effective to treat the subject suffering from an obstructive respiratory disease. In another embodiment, the compounds according to the invention include, inter alia, the compounds represented by the structures of the general formulae: (A), (I), (II), (III), (IV), (V), (VI), (VII), (VIII), (IX), (IXa), (IXb), (X), (XI), (XII), (XIII), (XIV), (XV), (XVI), (XVII), (XVIII), (XIX), (XX), (XXI), (XXII) or any combination thereof. In another embodiment, the obstructive respiratory disease is asthma. In another embodiment, the obstructive respiratory disease is rhinitis. In another embodiment, the obstructive respiratory disease is allergic rhinitis. In another embodiment, the obstructive respiratory disease is chronic obstructive pulmonary disease. In another embodiment, the invention provides a method of preventing asthma, rhinitis, allergic rhinitis, chronic obstructive pulmonary disease, obstructive respiratory disease, or a combination thereof, in a subject.

Illustrative of preferred Lipid-conjugates for use in the methods according to embodiments of this invention are those in which the lipid/phospholipid moiety is linked directly or indirectly through a bridging moiety listed below.

| phospholipid | spacer | polymer (m.w.) | abbreviation |
|---|---|---|---|
| PE | Dicarboxylic acid + Diamine | Polygeline (haemaccel) (4-40 kDa) | HeMPE; HemPE |
| PE | None | Carboxymethylcellulose (20-500 kDa) | CMPE; CMC-PE |

| phospholipid | spacer | polymer (m.w.) | abbreviation |
|---|---|---|---|
| PE | None | Hyaluronic acid (2-2000 kDa) | HYPE (HyPE) |
| PE | Dipalmitoic acid | Hyaluronic acid (2-2000 kDa) | HYPE-dipalmitoyl |
| PE | None | Polyethylene glycol | |
| PE | Y | Hydroxyethylstarch | HESPE; HesPE |
| PE | Dicarboxylic acid + Diamine | Dextran (1-2,000 kDa) | DexPE |
| PE | None | Dextran (1-2,000 kDa) | DexPE |
| PE | None | Albumin | |
| PE | None | Alginate (2-2000 kDa) | |
| PE | None | Polyaminoacid | |
| PE | None | Lactobionic acid | |
| PE | None | Acetylsalicylate | |
| PE | None | Cholesteryl-hemmisuccinate | |
| PE | None | Maltose | |
| PE | Y | None | Cholic acid |
| PE | None | Polycarboxylated polyethylene glycol | |
| PE | None | Heparin (0.5-110 kDa) | HEPPE; HEPE; HepPE |
| Dimyristoyl-PE | Y | Variable | DMPE |
| Dimyristoyl-PE | Y | Hyaluronic acid | HyDMPE |
| PS | Y | Polygeline (haemaccel) | |
| PS | Y | Heparin | |
| PS | Y | Hyaluronic acid | |
| PC | Y | Polygeline (haemaccel) | |
| PC | Y | Heparin | |
| PC | Y | Hyaluronic acid | |
| PI | Y | Polygeline (haemaccel) | |
| PI | Y | Heparin | |
| PI | Y | Hyaluronic acid | |
| PG | Y | Polygeline (haemaccel) | |
| PG | Y | Heparin | |
| PE | Y | Chondoitin sulfates | CSPE |
| PE | Y | Polygeline (haemaccel) | |
| PG | Y | Hyaluronic acid | |

In one embodiment of the invention, the compounds administered are HyPE, CSAPE, CMPE, HemPE, HesPE, DexPE and As-PE and pharmaceutically acceptable salts thereof, in combination with a physiologically acceptable carrier or solvent. These polymers, when chosen as the conjugated moiety, may vary in molecular weights from 200 to 2,000,000 Daltons. Various molecular weight species have been shown to have the desired biological efficacy, as shown in the section below.

In addition to the compounds of the Examples, further illustrative compounds of this invention are set forth in the section below.

Novel Compounds

Low molecular weight Lipid-conjugates, in which the conjugated moiety (X) is a monomer such as a salicylate, a bile acid, or cholesterylhemmisuccinate, or a di- or trisaccharide unit monomer of a polyglycosoaminoglycan such as heparin, heparan sulfate, chondroitin-6-sulfate, chondroitin-4-sulfate, hyaluronic acid, keratin, keratan sulfate, dermatin, or dermatan sulfate, have not been described before. According to embodiments of the invention, these new compounds display a similar biological activity profile as demonstrated below for the other Lipid-conjugates and have the general formula

[Phosphatidylethanolamine-Y]$_n$–X

[Phosphatidylserine-Y]$_n$–X

[Phosphatidylcholine-Y]$_n$–X

[Phosphatidylinositol-Y]$_n$–X

[Phosphatidylglycerol-Y]$_n$–X

[Phosphatidic acid-Y]$_n$–X

[lyso-phospholipid-Y]$_n$–X

[diacyl-glycerol-Y]$_n$–X

[monoacyl-glycerol-Y]$_n$—X

[sphingomyelin-Y]$_n$–X

[sphingosine-Y]$_n$–X

[ceramide-Y]$_n$—X wherein
Y is either nothing or a spacer group ranging in length from 2 to 30 atoms;
X is a mono- or disaccharide, carboxylated disaccharide, mono- or dicarboxylic acids, a salicylate, salicylic acid, aspirin, lactobionic acid, maltose, an amino acid, glycine, acetic acid, butyric acid, dicarboxylic acid, glutaric acid, succinic acid, fatty acid, dodecanoic acid, didodecanoic acid, bile acid, cholic acid, cholesterylhemmisuccinate, a di- or tripeptide, an oligopeptide, a trisacharide, or a di- or trisaccharide monomer unit of heparin, heparan sulfate, keratin, keratan sulfate, chondroitin, chondroitin-6-sulfate, chondroitin-4-sulfate, dermatin, dermatan sulfate, dextran, hyaluronic acid or glycosaminoglycan; and
n is the number of lipid moiety molecules bound to a molecule of X wherein n is a number from 1 to 100.

In another embodiment, the glycosaminoglycan is a polymer (X) of disaccharide units. In another embodiment, the number of the disaccharide units in the polymer is m. In another embodiment, m is a number from 2-10,000. In another embodiment, m is a number from 2-500. In another embodiment, m is a number from 2-1000. In another embodiment, m is a number from 50-500. In another embodiment, m is a number from 2-2000. In another embodiment, m is a number from 500-2000. In another embodiment, m is a number from 1000-2000. In another embodiment, m is a number from 2000-5000. In another embodiment, m is a number from 3000-7000. In another embodiment, m is a number from 5000-10,000. In another embodiment, a disaccharide unit of a glycosaminoglycan may be bound to one lipid or phospholipid moiety. In another embodiment, each disaccharide unit of the glycosaminoglycan may be bound to zero or one lipid or phospholipid moieties. In another embodiment, the lipid or phospholipid moieties are bound to the —COOH group of the disaccharide unit. In another embodiment, the bond between the lipid or phospholipid moiety and the disaccharide unit is an amide bond.

In one embodiment, this invention provides lipid-GAG conjugate or phospholipid-GAG conjugate of this invention, and methods of use thereof, wherein said conjugate represented by the structures of the general formulae (A), (I), (II), (III), (IV), (V), (VI), (VII), (VIII), (IX), (IXa), (IXb), (X), (Xa), (XI), (XII), (XIIa), (XIII), (XIV), (XV), (XVI), (XVII), (XVIII), (XIX), (XX), (XXI), and (XXII). In another embodiment, the average molecular weight of said GAG is between 5 kD to 90 kD. In another embodiment, the average molecular weight of said GAG is between 5 kD to 60 kD. In another embodiment, the average molecular weight of said GAG is between 5 kD to 40 kD. In another embodiment, the average molecular weight of said GAG is between 5 kD to 15 kD. In another embodiment, the average molecular weight of said GAG is between 5 kD to 20 kD. In another embodiment, the lipid-GAG conjugate is a phospholipid-GAG conjugate In one embodiment of this invention, low molecular weight phosphatidylethanolamine (PE)-conjugates are defined hereinabove as the compounds of formula (I) wherein:

$R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Y is either nothing or a spacer group ranging in length from 2 to 30 atoms;

X is a mono- or disaccharide, carboxylated disaccharide, mono- or dicarboxylic acids, a salicylate, salicylic acid, aspirin, lactobionic acid, maltose, an amino acid, glycine, acetic acid, butyric acid, dicarboxylic acid, glutaric acid, succinic acid, fatty acid, dodecanoic acid, didodecanoic acid, bile acid, cholic acid, cholesterylhemmisuccinate, a di- or tripeptide, an oligopeptide, a trisaccharide, or a di- or trisaccharide monomer unit of heparin, heparan sulfate, keratin, keratan sulfate, chondroitin, chondroitin-6-sulfate, chondroitin-4-sulfate, dermatin, dermatan sulfate, dextran, hyaluronic acid or glycosaminoglycan; and n is the number of lipid moity molecules bound to a molecule of X wherein n is a number from 1 to 1000.

In another embodiment, the molecular weight of said glycosaminoglycan is between 5 kD and 20 kD. In another embodiment, n is a number between 1 to 100. In another embodiment, said glycosaminoglycan is between 5 kD and 20 kD and n is between 1 to 100.

In one embodiment of this invention, low molecular weight phosphatidylserine (PS)-conjugates are defined hereinabove as the compounds of formula (II) wherein:

$R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Y is either nothing or a spacer group ranging in length from 2 to 30 atoms;

X is a mono- or disaccharide, carboxylated disaccharide, mono- or dicarboxylic acids, a salicylate, salicylic acid, aspirin, lactobionic acid, maltose, an amino acid, glycine, acetic acid, butyric acid, dicarboxylic acid, glutaric acid, succinic acid, fatty acid, dodecanoic acid, didodecanoic acid, bile acid, cholic acid, cholesterylhemmisuccinate, a di- or tripeptide, an oligopeptide, a trisaccharide, or a di- or trisaccharide monomer unit of heparin, heparan sulfate, keratin, keratan sulfate, chondroitin, chondroitin-6-sulfate, chondroitin-4-sulfate, dermatin, dermatan sulfate, dextran, hyaluronic acid or glycosaminoglycan; and n is the number of lipid moiety molecules bound to a molecule of X wherein n is a number from 1 to 1000.

In another embodiment, the molecular weight of said glycosaminoglycan is between 5 kD and 20 kD. In another embodiment, n is a number between 1 to 100. In another embodiment, said glycosaminoglycan is between 5 kD and 20 kD and n is between 1 to 100.

In one embodiment of this invention, Phosphatidylcholine (PC), Phosphatidylinositol (PI), and Phosphatidylglycerol (PG) conjugates are hereinabove defined as the compounds of formula (III) wherein:

$R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, inositol, choline, or glycerol;

Y is either nothing or a spacer group ranging in length from 2 to 30 atoms;

X is a mono- or disaccharide, carboxylated disaccharide, mono- or dicarboxylic acids, a salicylate, salicylic acid, aspirin, lactobionic acid, maltose, an amino acid, glycine, acetic acid, butyric acid, dicarboxylic acid, glutaric acid, succinic acid, fatty acid, dodecanoic acid, didodecanoic acid, bile acid, cholic acid, cholesterylhemmisuccinate, a di- or tripeptide, an oligopeptide, a trisaccharide, or a di- or trisaccharide monomer unit of heparin, heparan sulfate, keratin, keratan sulfate, chondroitin, chondroitin-6-sulfate, chondroitin-4-sulfate, dermatin, dermatan sulfate, dextran, hyaluronic acid or glycosaminoglycan; and n is the number of lipid moiety molecules bound to a molecule of X wherein n is a number from 1 to 1000.

In another embodiment, the molecular weight of said glycosaminoglycan is between 5 kD and 20 kD. In another embodiment, n is a number between 1 to 100. In another embodiment, said glycosaminoglycan is between 5 kD and 20 kD and n is between 1 to 100.

Examples of suitable divalent groups forming the optional bridging group Y are straight- or branched -chain alkylene, e.g., of 2 or more, preferably 4 to 18 carbon atoms, —CO-alkylene-CO, —NH-alkylene-NH—, —CO-alkylene-NH—, cycloalkylene, wherein alkylene in each instance, is straight or branched chain and contains 2 or more, preferably 2 to 18 carbon atoms in the chain, —(—O—CH(CH$_3$)CH$_2$—)$_x$— wherein x is an integer of 1 or more.

In another embodiment, in addition to the traditional phospholipid structure, related derivatives for use in this invention are phospholipids modified at the C1 or C2 position to contain an ether or alkyl bond instead of an ester bond. These derivatives are exemplified hereinabove by the general formulae (VIII) and (IX) wherein:

$R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, ethanolamine, serine, inositol, choline, or glycerol;

Y is either nothing or a spacer group ranging in length from 2 to 30 atoms;

X is a mono- or disaccharide, carboxylated disaccharide, mono- or dicarboxylic acids, a salicylate, salicylic acid, aspirin, lactobionic acid, maltose, an amino acid, glycine, acetic acid, butyric acid, dicarboxylic acid, glutaric acid, succinic acid, fatty acid, dodecanoic acid, didodecanoic acid, bile acid, cholic acid, cholesterylhemmisuccinate, a di- or tripeptide, an oligopeptide, a trisaccharide, or a di- or trisaccharide monomer unit of heparin, heparan sulfate, keratin, keratan sulfate, chondroitin, chondroitin-6-sulfate, chondroitin-4-sulfate, dermatin, dermatan sulfate, dextran, hyaluronic acid or glycosaminoglycan; and n is the number of lipid moiety molecules bound to a molecule of X wherein n is a number from 1 to 1000.

In another embodiment, the molecular weight of said glycosaminoglycan is between 5 kD and 20 kD. In another embodiment, n is a number between 1 to 100. In another embodiment, said glycosaminoglycan is between 5 kD and 20 kD and n is between 1 to 100.

In another embodiment, related low molecular weight derivatives for use in this invention are exemplified hereinabove by the general formulae (X), (XI) and (XII) wherein:

$R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, ethanolamine, serine, inositol, choline, or glycerol;

Y is either nothing or a spacer group ranging in length from 2 to 30 atoms;

X is a mono- or disaccharide, carboxylated disaccharide, mono- or dicarboxylic acids, a salicylate, salicylic acid, aspirin, lactobionic acid, maltose, an amino acid, glycine, acetic acid, butyric acid, dicarboxylic acid, glutaric acid, succinic acid, fatty acid, dodecanoic acid, didodecanoic acid, bile acid, cholic acid, cholesterylhemmisuccinate, a di- or tripeptide, an oligopeptide, a trisaccharide, or a di- or trisaccharide monomer unit of heparin, heparan sulfate, keratin, keratan sulfate, chondroitin, chondroitin-6-sulfate, chondroitin-4-sulfate, dermatin, dermatan sulfate, dextran, hyaluronic acid or glycosaminoglycan; and n is the number of lipid moiety molecules bound to a molecule of X wherein n is a number from 1 to 1000.

In another embodiment, the molecular weight of said glycosaminoglycan is between 5 kD and 20 kD. In another embodiment, n is a number between 1 to 100. In another embodiment, said glycosaminoglycan is between 5 kD and 20 kD and n is between 1 to 100.

In another embodiment, related low molecular weight derivatives for use in this invention are exemplified hereinabove by the general formulae (XIII) wherein:

$R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a mono- or disaccharide, carboxylated disaccharide, mono- or dicarboxylic acids, a salicylate, salicylic acid, aspirin, lactobionic acid, maltose, an amino acid, glycine, acetic acid, butyric acid, dicarboxylic acid, glutaric acid, succinic acid, fatty acid, dodecanoic acid, didodecanoic acid, bile acid, cholic acid, cholesterylhemmisuccinate, a di- or tripeptide, an oligopeptide, a trisaccharide, or a di- or trisaccharide monomer unit of heparin, heparan sulfate, keratin, keratan sulfate, chondroitin, chondroitin-6-sulfate, chondroitin-4-sulfate, dermatin, dermatan sulfate, dextran, hyaluronic acid or glycosaminoglycan; and n is the number of lipid moiety molecules bound to a molecule of X wherein n is a number from 1 to 1000.

In another embodiment, the molecular weight of said glycosaminoglycan is between 5 kD and 20 kD. In another embodiment, n is a number between 1 to 100. In another embodiment, said glycosaminoglycan is between 5 kD and 20 kD and n is between 1 to 100.

In another embodiment, related low molecular weight derivatives according to the invention may be exemplified herein by any of the general formulae (A), (I)-(XXI) wherein:

In one embodiment of the invention, X is covalently conjugated to a lipid. In another embodiment, x is covalently conjugated to a lipid via an amide bond. In another embodiment, x is covalently conjugated to a lipid via an esteric bond. In another embodiment, the lipid is phosphatidylethanolamine. In another embodiment, the GAG may be, inter alia, chondroitin sulfate. In another embodiment, the conjugate is biodegradable. In another embodiment, the glycosaminoglycan is between 5 kD and 20 kD.

In one embodiment, the invention provides glycosaminoglycans (GAG) compound covalently conjugated to a lipid to obtain a compound having preferred therapeutic properties. In another embodiment, the GAG compound is covalently conjugated to a lipid via an amide bond. In another embodiment, the GAG compound is covalently conjugated to a lipid via an esteric bond. In another embodiment, the lipid may be, inter alia, phosphatidylethanolamine. In another embodiment, the GAG may be, inter alia, chondroitin sulfate. In another embodiment, the conjugate is biodegradable. In another embodiment, the glycosaminoglycan is between 5 kD and 20 kD.

In one embodiment, this invention is directed to low molecular weight lipid-polymer conjugate comprising a GAG wherein the average molecular weight of said GAG is between 5 kd to 90 kd. In another embodiment, the average molecular weight of said GAG is between 5 kD to 60 kD. In another embodiment, the average molecular weight of said GAG is between 5 kD to 40 kD. In another embodiment, the average molecular weight of said GAG is between 5 kD to 15 kD. In another embodiment, the average molecular weight of said GAG is between 5 kD to 20 kD. In another embodiment, the average molecular weight of said GAG is between 5 kD to 25 kD.

Cell surface GAG play a key role in protecting cells from diverse damaging agents and processes, such as reactive oxygen species and free radicals, endotoxins, cytokines, invasion promoting enzymes, and agents that induce and/or facilitate degradation of extracellular matrix and basal membrane, cell invasiveness, white cell extravasation and infiltration, chemotaxis, and others. In addition, cell surface GAG protect cells from bacterial, viral and parasite infection, and their stripping exposes the cell to interaction and subsequent internalization of the microorganism. Enrichment of cell surface GAG would thus assist in protection of the cell from injurious processes. Thus, In one embodiment of the invention, PLA2 inhibitors were conjugated to GAGs or GAG-mimicking molecules. In another embodiment, these Lipid-conjugates, provides wide-range protection from diverse injurious processes, and are effective in amelioration of diseases that requires cell protection from injurous biochemical medistors.

In another embodiment, GAG-mimicking molecule may be, inter alia, a negatively charged molecule. In another embodiment, GAG-mimicking molecule may be, inter alia, a salicilate derivative. In another embodiment, GAG-mimicking molecule may be, inter alia, a dicarboxylic acid.

Preparation of Compounds

The preparation of some high molecular weight Lipid-conjugates is the subject of U.S. Pat. No. 5,064,817, which is incorporated herein by reference. These synthetic methods are reiterated below and are considered to be applicable as well to the preparation of low molecular, i.e. Lipid-conjugates comprising monomers and dimers as the conjugated moiety, with modifications in the procedure as readily evident to one skilled in the art.

When the starting compound chosen for the conjugated moiety has a substituent which is or can be rendered reactive to a substituent on the starting Lipid compound, the conjugated carrier moiety may be linked directly to lipid molecule(s) to produce the a Lipid-conjugate. When it does not, a bifunctional linking starting material can be used to link the two molecules indirectly.

Lipid-conjugates are prepared by linking a polar conjugate, e.g., a monomer or polymer, directly or indirectly to a PL moiety according to the general reaction schemes delineated in U.S. Pat. No. 5,064,817 and according to US Publication 2011-0130555.

For example, with acylated PE used as precursor for the PE conjugate, various lengths of dicarboxylic acids can be used as spacers. These acids can be linked to natural, semi-synthetic or synthetic PE.

For example, PE can be linked to aminodextran indirectly as delineated in U.S. Pat. No. 5,064,817 and US Publication 2011-0130555.

Polymers with carboxylic groups, such as polyamino acids, carboxymethyl cellulose or polymers to which fatty acids have been linked, can be linked directly to PE according to the scheme delineated in U.S. Pat. No. 5,064,817.

It is to be understood that these examples are given by way of illustration only and are not to be construed as limiting the invention either in spirit of in scope, as many modifications both in reagents and methods could be possible to those skilled in the art. Based on the wide spectrum of pharmacological properties exhibited by Lipid-conjugates, it is likely that compounds covered by Formula I-XXI, in addition to those explicitly described above, have the same valuable biological activities demonstrate to be useful in the methods of treating disease described below.

In one embodiment, the invention provides a process for the preparation of a compound represented by the structure of the general formula (A):

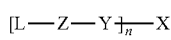

wherein

L is a lipid or a phospholipid;

Z is either nothing, ethanolamine, serine, inositol, choline, or glycerol;

Y is either nothing or a spacer group ranging in length from 2 to 30 atoms;

X is a physiologically acceptable monomer, dimer, oligomer, or polymer, wherein X is a glycosaminoglycan; and n is a number from 1 to 1000;

wherein any bond between L, Z, Y and X is either an amide or an esteric bond, including, inter alia, the steps of:

conjugating L to Z;

conjugating Z to Y;

conjugating Y to X;

wherein if Z is nothing, L is conjugated directly to Y, if Y is nothing, Z is conjugated directly to X, and if Y and Z are nothing, L is conjugated directly to X, thereby preparing a compound represented by the structure of the general formula (A).

In another embodiment, the invention provides a process for the preparation of a compound represented by the structure of the general formula (I):

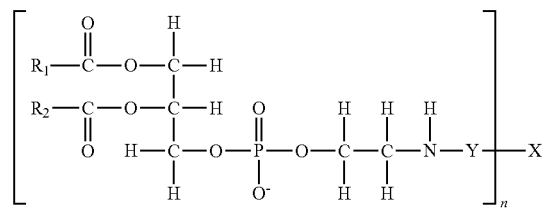

wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Y is either nothing or a spacer group ranging in length from 2 to 30 atoms;

X is either a physiologically acceptable monomer, dimer, oligomer or a physiologically acceptable polymer, wherein X is a glycosaminoglycan; and n is a number from 1 to 1,000;

wherein if Y is nothing the phosphatidylethanolamine is directly linked to X via an amide bond and if Y is a spacer, the spacer is directly linked to X via an amide or an esteric bond and to the phosphatidylethanolamine via an amide bond, including, inter alia, the steps of:

conjugating the phosphatidylethanolamine to Y; and conjugating Y to X;

if Y is nothing, the phosphatidylethanolamine is conjugated directly to X, thereby preparing a compound represented by the structure of the general formula (I).

In one embodiment of the invention, the phosphatidylethanolamine is the chemical moiety represented by the structure of:

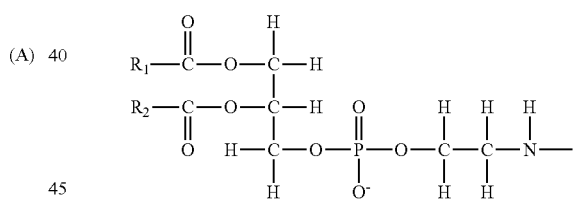

wherein $R_1$ and $R_2$ are defined herein.

In another embodiment, the invention provides a process for the preparation of a compound represented by the structure of the general formula (II):

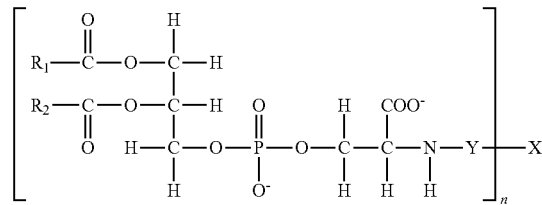

wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Y is either nothing or a spacer group ranging in length from 2 to 30 atoms;

X is a physiologically acceptable monomer, dimer, oligomer or polymer wherein x is a glycosaminoglycan; and n is a number from 1 to 1000;

wherein if Y is nothing the phosphatidylserine is directly linked to X via an amide bond and if Y is a spacer, the spacer is directly linked to X via an amide or an esteric bond and to the phosphatidylserine via an amide bond, including, inter alia, the steps of:

conjugating the phosphatidylserine to Y;

conjugating Y to X;

if Y is nothing, the phosphatidylserine is conjugated directly to X, thereby preparing a compound represented by the structure of the general formula (II).

In one embodiment of the invention, the phosphatidylserine is the chemical moiety represented by the structure of:

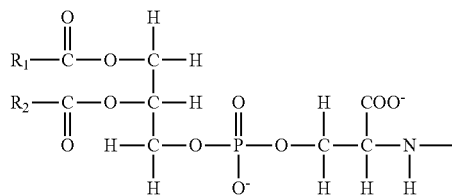

wherein $R_1$ and $R_2$ are defined herein.

In one embodiment, the invention provides a process for the preparation of a compound represented by the structure of the general formula (III):

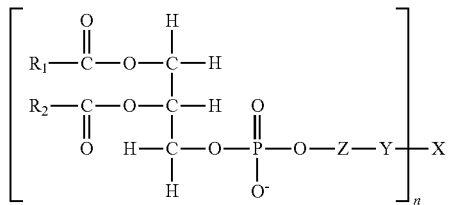

wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, inositol, choline, or glycerol;

Y is either nothing or a spacer group ranging in length from 2 to 30 atoms;

X is a physiologically acceptable monomer, dimer, oligomer, or polymer, wherein x is a glycosaminoglycan; and n is a number from 1 to 1000;

wherein any bond between the phosphatidyl, Z, Y and X is either an amide or anesteric bond, including, inter alia, the steps of:

conjugating the phosphatidyl to Z;

conjugating Z to Y;

conjugating Y to X;

wherein if Z is nothing, the phosphatidyl is conjugated directly to Y, if Y is nothing, Z is conjugated directly to X, and if Y and Z are nothing, the phosphatidyl is conjugated directly to X, thereby preparing a compound represented by the structure of the general formula (III).

In one embodiment of the invention, the phosphatidyl may be the chemical moiety represented by the structure of:

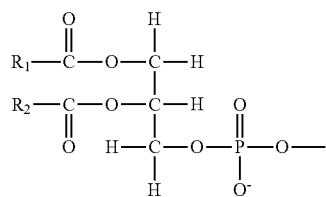

wherein $R_1$ and $R_2$ are defined herein.

In one embodiment, the invention provides a process for the preparation of a compound represented by the structure of the general formula (IV):

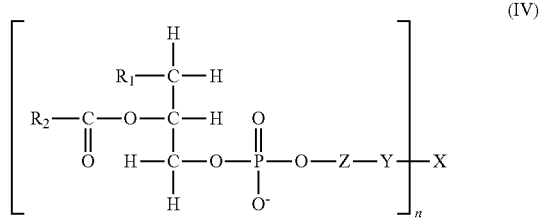

wherein $R_1$ is either hydrogen or a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, inositol, choline, or glycerol;

Y is either nothing or a spacer group ranging in length from 2 to 30 atoms;

X is a physiologically acceptable monomer, dimer, oligomer, or polymer, wherein x is a glycosaminoglycan; and n is a number from 1 to 1000;

wherein any bond between the phospholipid, Z, Y and X is either an amide or an esteric bond, including, inter alia, the steps of:

conjugating the phospholipid to Z;

conjugating Z to Y;

conjugating Y to X;

wherein if Z is nothing, the phospholipid is conjugated directly to Y, if Y is nothing, Z is conjugated directly to X, and if Y and Z are nothing, the phospholipid is conjugated directly to X, thereby preparing a compound represented by the structure of the general formula (IV).

In one embodiment of the invention, the phospholipid may be the chemical moiety represented by the structure of:

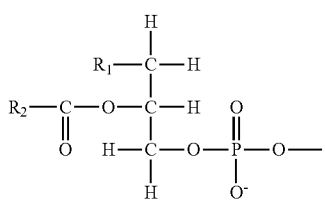

wherein $R_1$ and $R_2$ are defined herein.

In one embodiment, the invention provides a process for the preparation of a compound represented by the structure of the general formula (V):

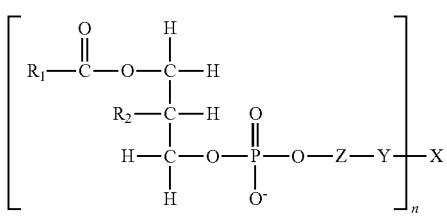

(V)

wherein
$R_1$ is a linear, saturated, mono-unsaturated, or poly-unsaturated, alkyl chain ranging in length from 2 to 30 carbon atoms;
$R_2$ is either hydrogen or a linear, saturated, mono-unsaturated, or poly-unsaturated, alkyl chain ranging in length from 2 to 30 carbon atoms;
Z is either nothing, inositol, choline, or glycerol;
Y is either nothing or a spacer group ranging in length from 2 to 30 atoms;
X is a physiologically acceptable monomer, dimer, oligomer, or polymer, wherein x is a glycosaminoglycan; and
n is a number from 1 to 1000;
wherein any bond between the phospholipid, Z, Y and X is either an amide or an esteric bond, including, inter alia, the steps of:
conjugating the phospholipid to Z;
conjugating Z to Y;
conjugating Y to X;
wherein if Z is nothing, the phospholipid is conjugated directly to Y, if Y is nothing, Z is conjugated directly to X, and if Y and Z are nothing, the phospholipid is conjugated directly to X, thereby preparing a compound represented by the structure of the general formula (V).

In one embodiment of the invention, the phospholipid may be the chemical moiety represented by the structure of:

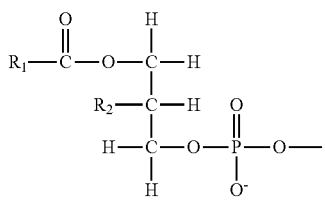

wherein $R_1$ and $R_2$ are defined herein.

In one embodiment, the invention provides a process for the preparation of a compound represented by the structure of the general formula (VI):

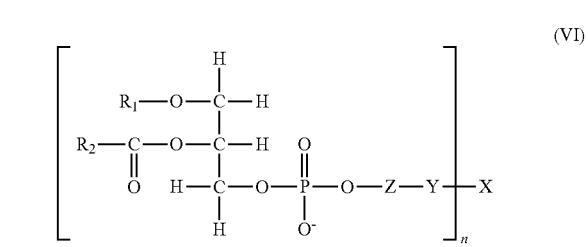

(VI)

wherein
$R_1$ is either hydrogen or a linear, saturated, mono-unsaturated, or poly-unsaturated, alkyl chain ranging in length from 2 to 30 carbon atoms;
$R_2$ is a linear, saturated, mono-unsaturated, or poly-unsaturated, alkyl chain ranging in length from 2 to 30 carbon atoms;
Z is either nothing, inositol, choline, or glycerol;
Y is either nothing or a spacer group ranging in length from 2 to 30 atoms;
X is a physiologically acceptable monomer, dimer, oligomer, or polymer, wherein x is a glycosaminoglycan; and
n is a number from 1 to 1000;
wherein any bond between the phospholipid, Z, Y and X is either an amide or an esteric bond, including, inter alia, the steps of:
conjugating the phospholipid to Z;
conjugating Z to Y;
conjugating Y to X;
wherein if Z is nothing, the phospholipid is conjugated directly to Y, if Y is nothing, Z is conjugated directly to X, and if Y and Z are nothing, the phospholipid is conjugated directly to X, thereby preparing a compound represented by the structure of the general formula (VI).

In one embodiment of the invention, the phospholipid may be the chemical moiety represented by the structure of:

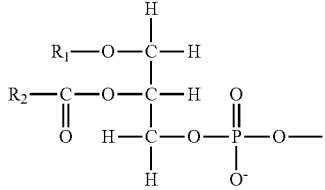

wherein $R_1$ and $R_2$ are defined herein.

In one embodiment, the invention provides a process for the preparation of a compound represented by the structure of the general formula (VII):

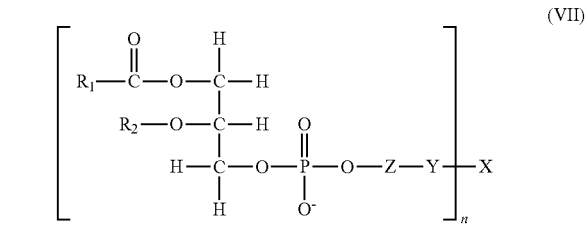

(VII)

wherein
$R_1$ is a linear, saturated, mono-unsaturated, or poly-unsaturated, alkyl chain ranging in length from 2 to 30 carbon atoms;
$R_2$ is either hydrogen or a linear, saturated, mono-unsaturated, or poly-unsaturated, alkyl chain ranging in length from 2 to 30 carbon atoms;
Z is either nothing, inositol, choline, or glycerol;
Y is either nothing or a spacer group ranging in length from 2 to 30 atoms;
X is a physiologically acceptable monomer, dimer, oligomer, or polymer, wherein x is a glycosaminoglycan; and
n is a number from 1 to 1000;
wherein any bond between the phospholipid, Z, Y and X is either an amide or an esteric bond, including, inter alia, the steps of:
conjugating the phospholipid to Z;
conjugating Z to Y;
conjugating Y to X;
wherein if Z is nothing, the phospholipid is conjugated directly to Y, if Y is nothing, Z is conjugated directly to X, and if Y and Z are nothing, the phospholipid is conjugated directly to X, thereby preparing a compound represented by the structure of the general formula (VII).

In one embodiment of the invention, the phospholipid may be the chemical moiety represented by the structure of:

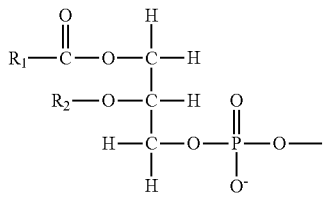

wherein $R_1$ and $R_2$ are defined herein.

In one embodiment, the invention provides a process for the preparation of a compound represented by the structure of the general formula (VIII):

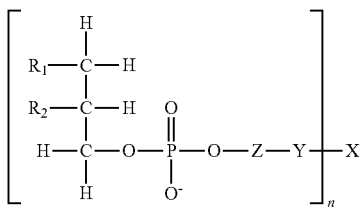

(VIII)

wherein
$R_1$ is a linear, saturated, mono-unsaturated, or poly-unsaturated, alkyl chain ranging in length from 2 to 30 carbon atoms;
$R_2$ is either hydrogen or a linear, saturated, mono-unsaturated, or poly-unsaturated, alkyl chain ranging in length from 2 to 30 carbon atoms;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer, wherein x is a glycosaminoglycan; and
n is a number from 1 to 1000;
wherein any bond between the phospholipid, Z, Y and X is either an amide or an esteric bond, including, inter alia, the steps of:
conjugating the phospholipid to Z;
conjugating Z to Y;
conjugating Y to X;
wherein if Z is nothing, the phospholipid is conjugated directly to Y, if Y is nothing, Z is conjugated directly to X, and if Y and Z are nothing, the phospholipid is conjugated directly to X, thereby preparing a compound represented by the structure of the general formula (VIII).

In one embodiment of the invention, the phospholipid may be the chemical moiety represented by the structure of:

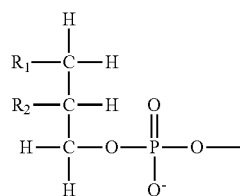

wherein $R_1$ and $R_2$ are defined herein.

In one embodiment, the invention provides a process for the preparation of a compound represented by the structure of the general formula (IX):

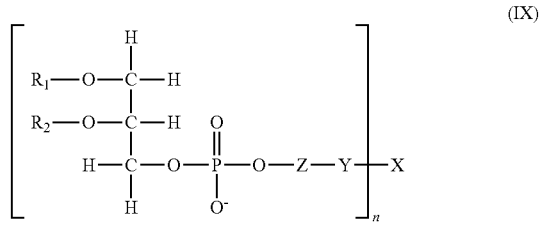

(IX)

wherein
$R_1$ is either hydrogen or a linear, saturated, mono-unsaturated, or poly-unsaturated, alkyl chain ranging in length from 2 to 30 carbon atoms;
$R_2$ is either hydrogen or a linear, saturated, mono-unsaturated, or poly-unsaturated, alkyl chain ranging in length from 2 to 30 carbon atoms;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer, wherein x is a glycosaminoglycan; and
n is a number from 1 to 1000;
wherein any bond between the phospholipid, Z, Y and X is either an amide or an esteric bond, including, inter alia, the steps of:
conjugating the phospholipid to Z;
conjugating Z to Y;
conjugating Y to X;
wherein if Z is nothing, the phospholipid is conjugated directly to Y, if Y is nothing, Z is conjugated directly to X, and if Y and Z are nothing, the phospholipid is conjugated directly to X, thereby preparing a compound represented by the structure of the general formula (IX).

In one embodiment of the invention, the phospholipid may be the chemical moiety represented by the structure of:

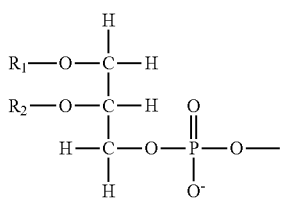

wherein $R_1$ and $R_2$ are defined herein.

In one embodiment, the invention provides a process for the preparation of a compound represented by the structure of the general formula (IXa):

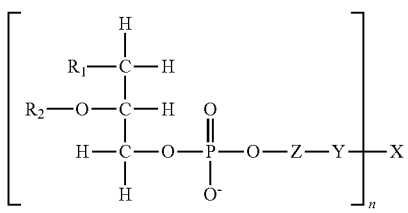

(IXa)

wherein
$R_1$ is either hydrogen or a linear, saturated, mono-unsaturated, or poly-unsaturated, alkyl chain ranging in length from 2 to 30 carbon atoms;
$R_2$ is either hydrogen or a linear, saturated, mono-unsaturated, or poly-unsaturated, alkyl chain ranging in length from 2 to 30 carbon atoms;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer, wherein x is a glycosaminoglycan; and
n is a number from 1 to 1000;
wherein any bond between the phospholipid, Z, Y and X is either an amide or an esteric bond, including, inter alia, the steps of:
conjugating the phospholipid to Z;
conjugating Z to Y;
conjugating Y to X;
wherein if Z is nothing, the phospholipid is conjugated directly to Y, if Y is nothing, Z is conjugated directly to X, and if Y and Z are nothing, the phospholipid is conjugated directly to X, thereby preparing a compound represented by the structure of the general formula (IXa).

In one embodiment of the invention, the phospholipid may be the chemical moiety represented by the structure of:

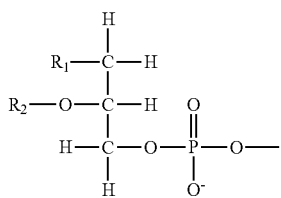

wherein $R_1$ and $R_2$ are defined herein.

In one embodiment, the invention provides a process for the preparation of a compound represented by the structure of the general formula (IXb):

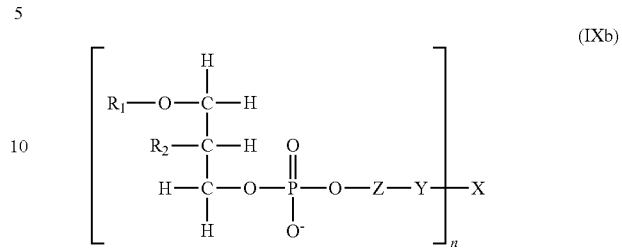

(IXb)

wherein
$R_1$ is either hydrogen or a linear, saturated, mono-unsaturated, or poly-unsaturated, alkyl chain ranging in length from 2 to 30 carbon atoms;
$R_2$ is either hydrogen or a linear, saturated, mono-unsaturated, or poly-unsaturated, alkyl chain ranging in length from 2 to 30 carbon atoms;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer, wherein x is a glycosaminoglycan; and
n is a number from 1 to 1000;
wherein any bond between the phospholipid, Z, Y and X is either an amide or an esteric bond, including, inter alia, the steps of:
conjugating the phospholipid to Z;
conjugating Z to Y;
conjugating Y to X;
wherein if Z is nothing, the phospholipid is conjugated directly to Y, if Y is nothing, Z is conjugated directly to X, and if Y and Z are nothing, the phospholipid is conjugated directly to X, thereby preparing a compound represented by the structure of the general formula (IXb).

In one embodiment of the invention, the phospholipid may be the chemical moiety represented by the structure of:

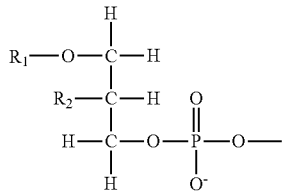

wherein $R_1$ and $R_2$ are defined herein.

In one embodiment, the invention provides a process for the preparation of a compound represented by the structure of the general formula (X):

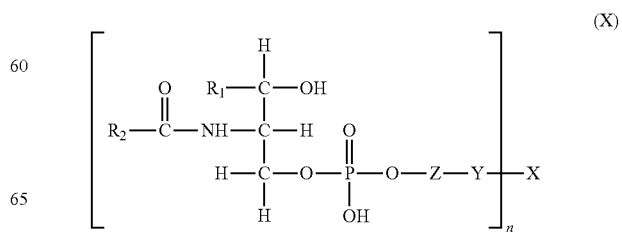

(X)

wherein $R_1$ is either hydrogen or a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing ethanolamine, serine, inositol, choline, or glycerol;

Y is either nothing or a spacer group ranging in length from 2 to 30 atoms;

X is a physiologically acceptable monomer, dimer, oligomer, or polymer, wherein x is a glycosaminoglycan; and n is a number from 1 to 1000;

wherein any bond between the ceramide phosphoryl, Z, Y and X is either an amide or an esteric bond, including, inter alia, the steps of:

conjugating the ceramide phosphoryl to Z;

conjugating Z to Y;

conjugating Y to X;

wherein if Z is nothing, the ceramide phosphoryl is conjugated directly to Y, if Y is nothing, Z is conjugated directly to X, and if Y and Z are nothing, the ceramide phosphoryl is conjugated directly to X, thereby preparing a compound represented by the structure of the general formula (X).

In one embodiment of the invention, the ceramide phosphoryl may be the chemical moiety represented by the structure of:

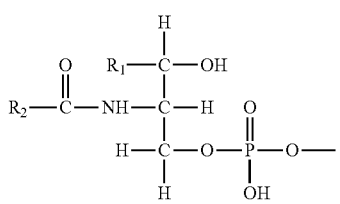

wherein $R_1$ and $R_2$ are defined herein.

In one embodiment, the invention provides a process for the preparation of a compound represented by the structure of the general formula (XI):

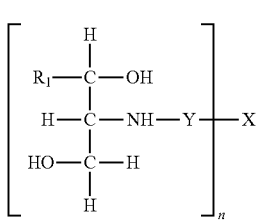

(XI)

wherein $R_1$ is a linear, saturated, mono-unsaturated, or poly-unsaturated, alkyl chain ranging in length from 2 to 30 carbon atoms;

Y is either nothing or a spacer group ranging in length from 2 to 30 atoms;

X is a physiologically acceptable monomer, dimer, oligomer or polymer, wherein x is a glycosaminoglycan; and n is a number from 1 to 1000;

wherein if Y is nothing the sphingosyl is directly linked to X via an amide bond and if Y is a spacer, the spacer is directly linked to X and to the sphingosyl via an amide bond and to X via an amide or an esteric bond, including, inter alia, the steps of:

conjugating the sphingosyl to Y;

conjugating Y to X;

wherein if Y is nothing, the sphingosyl is conjugated directly to X, thereby preparing a compound represented by the structure of the general formula (XI).

In one embodiment of the invention, the sphingosyl may be the chemical moiety represented by the structure of:

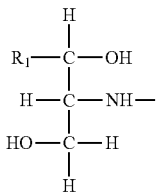

wherein $R_1$ is defined herein.

In one embodiment, the invention provides a process for the preparation of a compound represented by the structure of the general formula (XII):

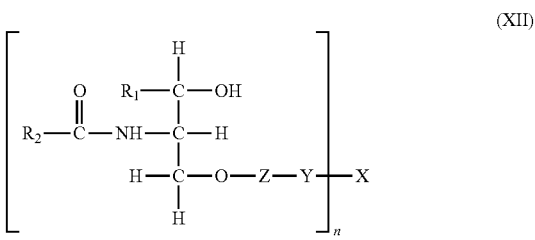

(XII)

wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

L is ceramide;

Z is either nothing, ethanolamine, serine, inositol, choline, or glycerol;

Y is either nothing or a spacer group ranging in length from 2 to 30 atoms;

X is a physiologically acceptable monomer, dimer, oligomer or polymer, wherein x is a glycosaminoglycan; and n is a number from 1 to 1000;

wherein any bond between the ceramide, Z, Y and X is either an amide or an esteric bond, including, inter alia, the steps of:

conjugating the ceramide to Z;

conjugating Z to Y;

conjugating Y to X;

wherein if Z is nothing, the ceramide is conjugated directly to Y, if Y is nothing, Z is conjugated directly to X, and if Y and Z are nothing, the ceramide is conjugated directly to X, thereby preparing a compound represented by the structure of the general formula (XII).

In one embodiment of the invention, the ceramide may be the chemical moiety represented by the structure of:

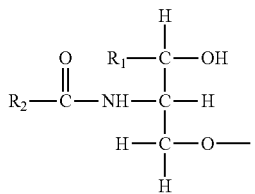

wherein $R_1$ and $R_2$ are defined herein.

In one embodiment, the invention provides a process for the preparation of a compound represented by the structure of the general formula (XIII):

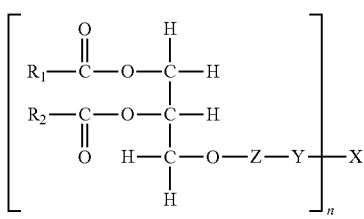

(XIII)

wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a physiologically acceptable monomer, dimer, oligomer or polymer, wherein x is a glycosaminoglycan; and n is a number from 1 to 1000;

wherein any bond between the diglyceryl, Z, Y and X is either an amide or an esteric bond, including, inter alia, the steps of:

conjugating the diglyceryl to Z;
conjugating Z to Y;
conjugating Y to X;
wherein if Z is nothing, the diglyceryl is conjugated directly to Y, if Y is nothing, Z is conjugated directly to X, and if Y and Z are nothing, the diglyceryl is conjugated directly to X, thereby preparing a compound represented by the structure of the general formula (XIII).

In one embodiment of the invention, the diglyceryl may be the chemical moiety represented by the structure of:

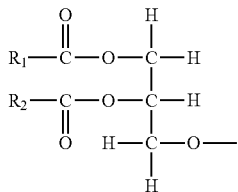

wherein $R_1$ and $R_2$ are defined herein.

In one embodiment, the invention provides a process for the preparation of a compound represented by the structure of the general formula (XIV):

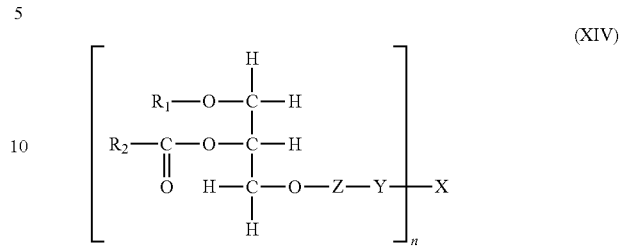

(XIV)

wherein $R_1$ is either hydrogen or a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a physiologically acceptable monomer, dimer, oligomer or polymer, wherein x is a glycosaminoglycan; and n is a number from 1 to 1000;

wherein any bond between the glycerolipid, Z, Y and X is either an amide or an esteric bond, including, inter alia, the steps of:

conjugating the glycerolipid to Z;
conjugating Z to Y;
conjugating Y to X;
wherein if Z is nothing, the glycerolipid is conjugated directly to Y, if Y is nothing, Z is conjugated directly to X, and if Y and Z are nothing, the glycerolipid is conjugated directly to X, thereby preparing a compound represented by the structure of the general formula (XIV).

In one embodiment of the invention, the glycerolipid may be the chemical moiety represented by the structure of:

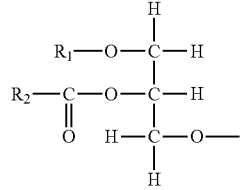

wherein $R_1$ and $R_2$ are defined herein.

In one embodiment, the invention provides a process for the preparation of a compound represented by the structure of the general formula (XV):

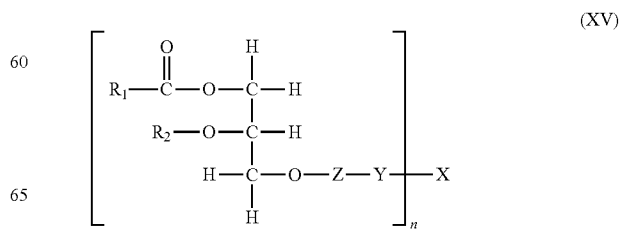

(XV)

wherein

R$_1$ is a linear, saturated, mono-unsaturated, or poly-unsaturated, alkyl chain ranging in length from 2 to 30 carbon atoms;

R$_2$ is either hydrogen or a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a physiologically acceptable monomer, dimer, oligomer or polymer, wherein x is a glycosaminoglycan; and n is a number from 1 to 1000;

wherein any bond between the glycerolipid, Z, Y and X is either an amide or an esteric bond, including, inter alia, the steps of:

conjugating the glycerolipid to Z;

conjugating Z to Y;

conjugating Y to X;

wherein if Z is nothing, the glycerolipid is conjugated directly to Y, if Y is nothing, Z is conjugated directly to X, and if Y and Z are nothing, the glycerolipid is conjugated directly to X, thereby preparing a compound represented by the structure of the general formula (XV).

In one embodiment of the invention, the glycerolipid may be the chemical moiety represented by the structure of:

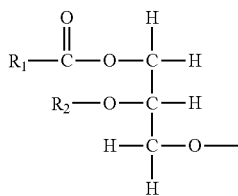

wherein R$_1$ and R$_2$ are defined herein.

In one embodiment, the invention provides a process for the preparation of a compound represented by the structure of the general formula (XVI):

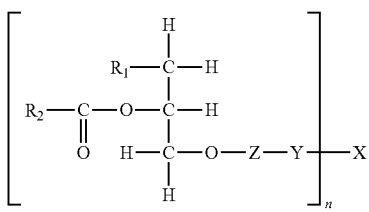

(XVI)

wherein

R$_1$ is either hydrogen or a linear, saturated, mono-unsaturated, or poly-unsaturated, alkyl chain ranging in length from 2 to 30 carbon atoms;

R$_2$ is a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a physiologically acceptable monomer, dimer, oligomer or polymer, wherein x is a glycosaminoglycan; and n is a number from 1 to 1000;

wherein any bond between the lipid, Z, Y and X is either an amide or an esteric bond, including, inter alia, the steps of:

conjugating the lipid to Z;

conjugating Z to Y;

conjugating Y to X;

wherein if Z is nothing, the lipid is conjugated directly to Y, if Y is nothing, Z is conjugated directly to X, and if Y and Z are nothing, the lipid is conjugated directly to X, thereby preparing a compound represented by the structure of the general formula (XVI).

In one embodiment of the invention, the lipid may be the chemical moiety represented by the structure of:

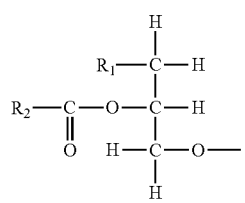

wherein R$_1$ and R$_2$ are defined herein.

In one embodiment, the invention provides a process for the preparation of a compound represented by the structure of the general formula (XVII):

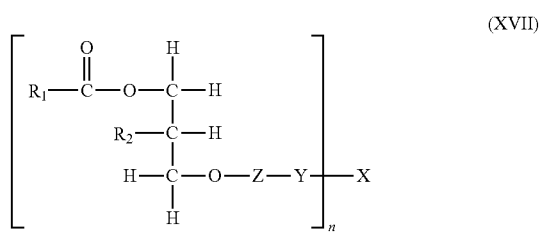

(XVII)

wherein

R$_1$ is either hydrogen or a linear, saturated, mono-unsaturated, or poly-unsaturated, alkyl chain ranging in length from 2 to 30 carbon atoms;

R$_2$ is a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a physiologically acceptable monomer, dimer, oligomer or polymer, wherein x is a glycosaminoglycan; and n is a number from 1 to 1000;

wherein any bond between the lipid, Z, Y and X is either an amide or an esteric bond, including, inter alia, the steps of:

conjugating the lipid to Z;

conjugating Z to Y;

conjugating Y to X;

wherein if Z is nothing, the lipid is conjugated directly to Y, if Y is nothing, Z is conjugated directly to X, and if Y and Z are nothing, the lipid is conjugated directly to X, thereby preparing a compound represented by the structure of the general formula (XVII).

In one embodiment of the invention, the lipid may be the chemical moiety represented by the structure of:

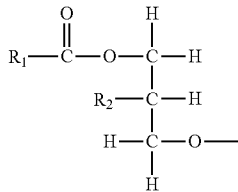

wherein $R_1$ and $R_2$ are defined herein.

In one embodiment, the invention provides a process for the preparation of a compound represented by the structure of the general formula (XVIII):

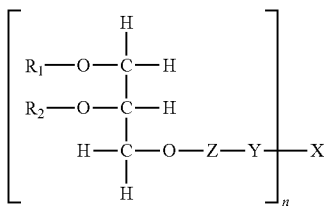

(XVIII)

wherein
$R_1$ is either hydrogen or a linear, saturated, mono-unsaturated, or poly-unsaturated, alkyl chain ranging in length from 2 to 30 carbon atoms;
$R_2$ is either hydrogen or a linear, saturated, mono-unsaturated, or poly-unsaturated, alkyl chain ranging in length from 2 to 30 carbon atoms;
Z is either nothing, choline, phosphate, inositol, or glycerol;
Y is either nothing or a spacer group ranging in length from 2 to 30 atoms;
X is a physiologically acceptable monomer, dimer, oligomer or polymer, wherein x is a glycosaminoglycan; and
n is a number from 1 to 1000;
wherein any bond between the lipid, Z, Y and X is either an amide or an esteric bond, including, inter alia, the steps of:
conjugating the lipid to Z;
conjugating Z to Y;
conjugating Y to X;
wherein if Z is nothing, the lipid is conjugated directly to Y, if Y is nothing, Z is conjugated directly to X, and if Y and Z are nothing, the lipid is conjugated directly to X, thereby preparing a compound represented by the structure of the general formula (XVIII).

In one embodiment of the invention, the lipid may be the chemical moiety represented by the structure of:

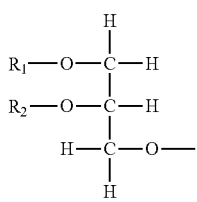

wherein $R_1$ and $R_2$ are defined herein.

In one embodiment, the invention provides a process for the preparation of a compound represented by the structure of the general formula (XIX):

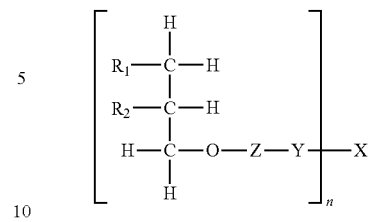

(XIX)

wherein
is $R_1$ is either hydrogen or a linear, saturated, mono-unsaturated, or poly-unsaturated, alkyl chain ranging in length from 2 to 30 carbon atoms;
$R_2$ is either hydrogen or a linear, saturated, mono-unsaturated, or poly-unsaturated, alkyl chain ranging in length from 2 to 30 carbon atoms;
Z is either nothing, choline, phosphate, inositol, or glycerol;
Y is either nothing or a spacer group ranging in length from 2 to 30 atoms;
X is a physiologically acceptable monomer, dimer, oligomer or polymer, wherein x is a glycosaminoglycan; and
n is a number from 1 to 1000;
wherein any bond between the lipid, Z, Y and X is either an amide or an esteric bond, including, inter alia, the steps of:
conjugating the lipid to Z;
conjugating Z to Y;
conjugating Y to X;
wherein if Z is nothing, the lipid is conjugated directly to Y, if Y is nothing, Z is conjugated directly to X, and if Y and Z are nothing, the lipid is conjugated directly to X, thereby preparing a compound represented by the structure of the general formula (XIX).

In one embodiment of the invention, the lipid may be the chemical moiety represented by the structure of:

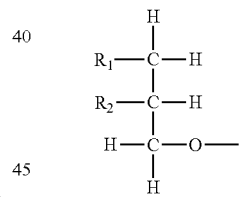

wherein $R_1$ and $R_2$ are defined herein.

In one embodiment, the invention provides a process for the preparation of a compound represented by the structure of the general formula (XX):

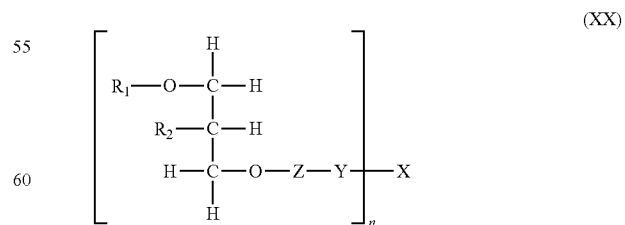

(XX)

wherein
$R_1$ is either hydrogen or a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a physiologically acceptable monomer, dimer, oligomer or polymer, wherein x is a glycosaminoglycan; and n is a number from 1 to 1000;

wherein any bond between the lipid, Z, Y and X is either an amide or an esteric bond, including, inter alia, the steps of:

conjugating the lipid to Z;

conjugating Z to Y;

conjugating Y to X;

wherein if Z is nothing, the lipid is conjugated directly to Y, if Y is nothing, Z is conjugated directly to X, and if Y and Z are nothing, the lipid is conjugated directly to X, thereby preparing a compound represented by the structure of the general formula (XX).

In one embodiment of the invention, the lipid may be the chemical moiety represented by the structure of:

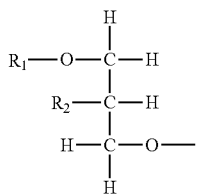

wherein $R_1$ and $R_2$ are defined herein.

In one embodiment, the invention provides a process for the preparation of a compound represented by the structure of the general formula (XXI):

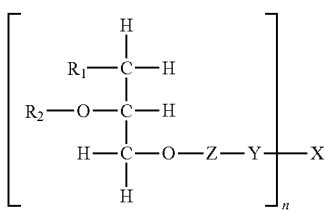

(XXI)

wherein $R_1$ is either hydrogen or a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a physiologically acceptable monomer, dimer, oligomer or polymer, wherein x is a glycosaminoglycan; and n is a number from 1 to 1000;

wherein any bond between the lipid, Z, Y and X is either an amide or an esteric bond, including, inter alia, the steps of:

conjugating the lipid to Z;

conjugating Z to Y;

conjugating Y to X;

wherein if Z is nothing, the lipid is conjugated directly to Y, if Y is nothing, Z is conjugated directly to X, and if Y and Z are nothing, the lipid is conjugated directly to X, thereby preparing a compound represented by the structure of the general formula (XXI).

In one embodiment of the invention, the lipid may be the chemical moiety represented by the structure of:

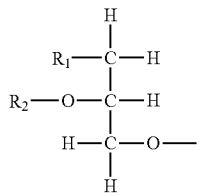

wherein $R_1$ and $R_2$ are defined herein.

In another embodiment, the conjugating according to the invention may be performed by eliminating a water molecule, thereby forming amide or esteric bonds. In another embodiment, the conjugating may be performed in the presence of a detergent. In another embodiment, the conjugating may be induced by ultrasonic radiation.

In another embodiment, any conjugation process according to the invention may be performed by eliminating a water molecule, thereby forming amide or esteric bonds. In another embodiment, any conjugation process according to the invention may be performed in the presence of a detergent. In another embodiment, any conjugation process according to the invention may be induced by ultrasonic radiation.

In another embodiment, any compound according to the invention may be prepared by a conjugation process performed by eliminating a water molecule, thereby forming amide or esteric bonds. In another embodiment, any compound according to the invention may be prepared by a conjugation process in the presence of a detergent. In another embodiment, any compound according to the invention may be prepared by a conjugation process induced by ultrasonic radiation.

In one embodiment of the invention, the conjugation of the phosphatidylethanolamine and chondroitin sulfate is performed in the presence of a detergent. In another embodiment a detergent may be, inter alia, DDAB. Of course any other appropriate detergent may be used.

In one embodiment of the invention, the conjugation of the phosphatidylethanolamine and hyaluronic acid is induced by sonication.

Methods of Treating Disease Based on PL Conjugates

In one embodiment of the invention, the Lipid-conjugates described herein can be used to treat disease, through exerting at least one of their many pharmacological activities, among which are amelioration, or prevention, of tissue injury arising in the course of pathological disease states by stabilizing cell membranes; limiting oxidative damage to cell and blood components; limiting cell proliferation, cell extravasation and (tumor) cell migratory behavior; suppressing immune responses; or attenuating physiological reactions to stress, as expressed in elevated chemokine levels. The medicinal properties of these compounds are readily exemplified in using animal models of the particular disease in which it is desired to use the drug. The patients to whom the lipid or PL conjugates should be administered are those that are experiencing symptoms of disease or who are at risk of contracting the disease or experiencing a recurrent episode or exacerbation of the disease. The efficacy of these compounds in cellular and animal models of disease are described below in The Examples.

The combination of lipids, such as, but not limited to phosphatidylethanolamine and phosphatidylserine, with additional monomer or polymer moieties, is thus a practical route to the production of new drugs for medical purposes, provided that the resultant chemical composition displays the desired range of pharmacological properties. In the cases described herein, the diversity of biological activities and the effectiveness in disease exhibited by the compounds far exceed the properties anticipated by use of the starting materials themselves, when administered alone or in combination. However, it is likely that the PL conjugate compounds, alone or in combination, will prove to be valuable drugs when adapted to methods of disease treatment other to those conditions specifically described herein.

In one embodiment, the invention provides a method of treating a subject afflicted with a disease related to chronic rhinosinusitis, nasal polyps.

In one embodiment, the invention provides a method of treating a subject suffering from chronic rhinosinusitis, including, inter alia, the step of administering to a subject an effective amount of a lipid or phospholipid moiety bonded to a physiologically acceptable monomer, dimer, oligomer, or polymer.

In one embodiment, the invention provides a method of preventing chronic rhinosinusitis in a subject, including, inter alia, the step of administering to a subject an effective amount of a lipid or phospholipid moiety bonded to a physiologically acceptable monomer, dimer, oligomer, or polymer.

In one embodiment, the invention provides a method of treating a subject suffering from nasal polyps, including, inter alia, the step of administering to a subject an effective amount of a lipid or phospholipid moiety bonded to a physiologically acceptable monomer, dimer, oligomer, or polymer.

In one embodiment, the invention provides a method of preventing nasal polyps in a subject, including, inter alia, the step of administering to a subject an effective amount of a lipid or phospholipid moiety bonded to a physiologically acceptable monomer, dimer, oligomer, or polymer.

In one embodiment, the invention provides a use of a lipid or phospholipid moiety bonded to a physiologically acceptable monomer, dimer, oligomer, or polymer, in the preparation of a pharmaceutical composition for treating a subject suffering from chronic rhinosinusitis.

In one embodiment, the invention provides a use of a lipid or phospholipid moiety bonded to a physiologically acceptable monomer, dimer, oligomer, or polymer, in the preparation of a pharmaceutical composition for preventing chronic rhinosinusitis in a subject.

In one embodiment, the invention provides a use of a lipid or phospholipid moiety bonded to a physiologically acceptable monomer, dimer, oligomer, or polymer, in the preparation of a pharmaceutical composition for treating a subject suffering from nasal polyps.

In one embodiment, the invention provides a use of a lipid or phospholipid moiety bonded to a physiologically acceptable monomer, dimer, oligomer, or polymer, in the preparation of a pharmaceutical composition for preventing nasal polyps in a subject.

In one embodiment of the invention, the treatment requires controlling the expression, production, and activity of phospholipase enzymes. In another embodiment, the treatment requires controlling the production and/or action of lipid mediators. In another embodiment, the treatment requires amelioration of damage to glycosaminoglycans (GAG) and proteoglycans. In another embodiment, the treatment requires controlling the production and action of oxidants, oxygen radicals and nitric oxide. In another embodiment, the treatment requires anti-oxidant therapy. In another embodiment, the treatment requires anti-endotoxin therapy. In another embodiment, the treatment requires controlling the expression, production or action of cytokines, chemokines, adhesion molecules or interleukines. In another embodiment, the treatment requires protection of lipoproteins from damaging agents. In another embodiment, the treatment requires controlling the proliferation of cells. In another embodiment, the treatment requires controlling of angiogenesis and organ vascularization. In another embodiment, the treatment requires inhibition of invasion-promoting enzymes. In another embodiment, the treatment requires controlling of cell invasion. In another embodiment, the invading cells are white blood cells. In another embodiment, the invading cells are cancer cells. In another embodiment, the treatment requires controlling of white cell activation, adhesion or extravasation. In another embodiment, the treatment requires amelioration of ischemia or reperfusion injury. In another embodiment, the treatment requires inhibition of lymphocyte activation. In another embodiment, the treatment requires protection of blood brain barrier. In another embodiment, the treatment requires control of neurotransmitter production and action. In another embodiment, the treatment requires controlling of blood vessel and airway contraction. In another embodiment, the treatment requires extracorporeal tissue preservation.

In one embodiment of the invention, the lipid mediator is a glycerolipid. In another embodiment, the lipid mediator is a phospholipid. In another embodiment, the lipid mediator is sphingolipid. In another embodiment, the lipid mediator is a sphingosine. In another embodiment, the lipid mediator is ceramide. In another embodiment, the lipid mediator is a fatty acid. In another embodiment, the fatty acid is arachidonic acid. In another embodiment, the lipid mediator is an arachidonic acid-derived eicosanoid. In another embodiment, the lipid mediator is a platelet activating factor (PAF). In another embodiment, the lipid mediator is a lysophospholipid.

In one embodiment of the invention, the damaging agent is a phospholipase. In another embodiment, the damaging agent is a reactive oxygen species (ROS). In another embodiment, the damaging agent is a free radical. In another embodiment, the damaging agent is a lysophospholipid. In another embodiment, the damaging agent is a fatty acid or a derivative thereof. In another embodiment, the damaging agent is hydrogen peroxide. In another embodiment, the damaging agent is a phospholipid. In another embodiment, the damaging agent is an oxidant. In another embodiment, the damaging agent is a cationic protein. In another embodiment, the damaging agent is a streptolysin. In another embodiment, the damaging agent is a protease. In another embodiment, the damaging agent is a hemolysin. In another embodiment, the damaging agent is a sialidase.

In one embodiment of the invention, the invasion-promoting enzyme is collagenase. In another embodiment, the invasion-promoting enzyme is matrix-metaloproteinase (MMP). In another embodiment, the invasion-promoting enzyme is heparinase. In another embodiment, the invasion-promoting enzyme is heparanase. In another embodiment, the invasion-promoting enzyme is hyaluronidase. In another embodiment, the invasion-promoting enzyme is gelatinase. In another embodiment, the invasion-promoting enzyme is chondroitinase. In another embodiment, the invasion-promoting enzyme is dermatanase. In another embodiment, the invasion-promoting enzyme is keratanase. In another embodiment, the invasion-promoting enzyme is protease. In another embodiment, the invasion-promoting enzyme is lyase. In another embodiment, the invasion-promoting enzyme is hydrolase. In another embodiment, the invasion-promoting enzyme is a glycosaminoglycan degrading enzyme. In another embodiment, the invasion-promoting enzyme is a proteoglycan degrading enzyme.

In one embodiment of the invention, the physiologically acceptable monomer is salicylate. In another embodiment, the physiologically acceptable monomer is salicylic acid. In another embodiment, the physiologically acceptable monomer is aspirin. In another embodiment, the physiologically acceptable monomer is a monosaccharide. In another embodiment, the physiologically acceptable monomer is lactobionic acid. In another embodiment, the physiologically acceptable monomer is glucoronic acid. In another embodiment, the physiologically acceptable monomer is maltose. In another embodiment, the physiologically acceptable monomer is an amino acid. In another embodiment, the physiologically acceptable monomer is glycine. In another embodiment, the physiologically acceptable monomer is a carboxylic acid. In another embodiment, the physiologically acceptable monomer is an acetic acid. In another embodiment, the physiologically acceptable monomer is a butyric acid. In another embodiment, the physiologically acceptable monomer is a dicarboxylic acid. In another embodiment, the physiologically acceptable monomer is a glutaric acid. In another embodiment, the physiologically acceptable monomer is succinic acid. In another embodiment, the physiologically acceptable monomer is a fatty acid. In another embodiment, the physiologically acceptable monomer is dodecanoic acid. In another embodiment, the physiologically acceptable monomer is didodecanoic acid. In another embodiment, the physiologically acceptable monomer is bile acid. In another embodiment, the physiologically acceptable monomer is cholic acid. In another embodiment, the physiologically acceptable monomer is cholesterylhemmisuccinate.

In one embodiment of the invention, the physiologically acceptable dimer or oligomer is physiologically acceptable dimer or oligomer is a dipeptide. In another embodiment, the physiologically acceptable dimer or oligomer is a disaccharide. In another embodiment, the physiologically acceptable dimer or oligomer is a trisaccharide. In another embodiment, the physiologically acceptable dimer or oligomer is an oligosaccharide. In another embodiment, the physiologically acceptable dimer or oligomer is an oligopeptide. In another embodiment, the physiologically acceptable dimer or oligomer is a di- or trisaccharide monomer unit of glycosaminoglycans. In another embodiment, the physiologically acceptable dimer or oligomer is hyaluronic acid. In another embodiment, the physiologically acceptable dimer or oligomer is heparin. In another embodiment, the physiologically acceptable dimer or oligomer is heparan sulfate. In another embodiment, the physiologically acceptable dimer or oligomer is keratin. In another embodiment, the physiologically acceptable dimer or oligomer is keratan sulfate. In another embodiment, the physiologically acceptable dimer or oligomer is chondroitin. In another embodiment, the chondroitin is chondroitin sulfate. In another embodiment, the chondroitin is chondroitin-4-sulfate. In another embodiment, the chondroitin is chondroitin-6-sulfate. In another embodiment, the physiologically acceptable dimer or oligomer is dermatin. In another embodiment, the physiologically acceptable dimer or oligomer is dermatan sulfate. In another embodiment, the physiologically acceptable dimer or oligomer is dextran. In another embodiment, the physiologically acceptable dimer or oligomer is polygeline ('Haemaccel'). In another embodiment, the physiologically acceptable dimer or oligomer is alginate. In another embodiment, the physiologically acceptable dimer or oligomer is hydroxyethyl starch (Hetastarch). In another embodiment, the physiologically acceptable dimer or oligomer is ethylene glycol. In another embodiment, the physiologically acceptable dimer or oligomer is carboxylated ethylene glycol.

In one embodiment of the invention, the physiologically acceptable polymer is a glycosaminoglycan. In another embodiment, the physiologically acceptable polymer is hyaluronic acid. In another embodiment, the physiologically acceptable polymer is heparin. In another embodiment, the physiologically acceptable polymer is heparan sulfate. In another embodiment, the physiologically acceptable polymer is chondroitin. In another embodiment, the chondroitin is chondroitin-4-sulfate. In another embodiment, the chondroitin is chondroitin-6-sulfate. In another embodiment, the physiologically acceptable polymer is keratin. In another embodiment, the physiologically acceptable polymer is keratan sulfate. In another embodiment, the physiologically acceptable polymer is dermatin. In another embodiment, the physiologically acceptable polymer is dermatan sulfate. In another embodiment, the physiologically acceptable polymer is carboxymethylcellulose. In another embodiment, the physiologically acceptable polymer is dextran. In another embodiment, the physiologically acceptable polymer is polygeline ('Haemaccel'). In another embodiment, the physiologically acceptable polymer is alginate. In another embodiment, the physiologically acceptable polymer is hydroxyethyl starch ('Hetastarch'). In another embodiment, the physiologically acceptable polymer is polyethylene glycol. In another embodiment, the physiologically acceptable polymer is polycarboxylated polyethylene glycol.

In one embodiment of the invention, the lipid or phospholipid moiety is phosphatidic acid. In another embodiment, lipid or phospholipid moiety is an acyl glycerol. In another embodiment, lipid or phospholipid moiety is monoacylglycerol. In another embodiment, lipid or phospholipid moiety is diacylglycerol. In another embodiment, lipid or phospholipid moiety is triacylglycerol. In another embodiment, lipid or phospholipid moiety is sphingosine. In another embodiment, lipid or phospholipid moiety is sphingomyelin. In another embodiment, lipid or phospholipid moiety is ceramide. In another embodiment, lipid or phospholipid moiety is phosphatidylethanolamine. In another embodiment, lipid or phospholipid moiety is phosphatidylserine. In another embodiment, lipid or phospholipid moiety is phosphatidylcholine. In another embodiment, lipid or phospholipid moiety is phosphatidylinositol. In another embodiment, lipid or phospholipid moiety is phosphatidylglycerol. In another embodiment, lipid or phospholipid moiety is an ether or alkyl phospholipid derivative thereof.

In one embodiment, the invention provides a method of treating a subject afflicted with a disease, wherein the treatment of the disease requires controlling phospholipase A2 activities; controlling the production and/or action of lipid mediators, such as eicosanoids, platelet activating factor (PAF) and lyso-phospholipids; amelioration of damage to cell surface glycosaminoglycans (GAG) and proteoglycans; controlling the production of oxygen radicals and nitric oxide; protection of cells, tissues, and plasma lipoproteins from damaging agents, such as reactive oxygen species (ROS) and phospholipases; anti-oxidant therapy; anti-endotoxin therapy; controlling of cytokine, chemokine and interleukine production; controlling the proliferation of cells, including smooth muscle cells, endothelial cells and skin fibroblasts; controlling of angiogenesis and organ vascularization; inhibition of invasion-promoting enzymes, such as collagenase, heparinase, heparanase and hyaluronidase; controlling of cell invasion; controlling of white cell activation, adhesion and extravasation; amelioration of ischemia/reperfusion injury, inhibition of lymphocyte activation; controlling of blood vessel and airway contraction; protection of blood brain barrier; controlling of neurotransmitter (e.g., dopamine) production and action (e.g., acetylcholine); extracorporeal tissue preservation or any combination thereof.

In one embodiment of the invention, the term "controlling" refers to inhibiting the production and action of the above mentioned factors in order to maintain their activity at the normal basal level and suppress their activation in pathological conditions.

In one embodiment of the invention, the physiologically acceptable monomer is either a salicylate, salicylic acid, aspirin, a monosaccharide, lactobionic acid, maltose, an amino acid, glycine, carboxylic acid, acetic acid, butyric acid, dicarboxylic acid, glutaric acid, succinic acid, fatty acid, dodecanoic acid, didodecanoic acid, bile acid, cholic acid, cholesterylhemmisuccinate; or wherein the physiologically acceptable dimer or oligomer is a dipeptide, a disaccharide, a trisaccharide, an oligopeptide, or a di- or trisaccharide monomer unit of heparin, heparan sulfate, keratin, keratan sulfate, chondroitin, chondroitin-6-sulfate, chondroitin-4-sulfate, dermatin, dermatan sulfate, dextran, or hyaluronic acid; or wherein the physiologically acceptable polymer is a glycosaminoglycan, polygelin ('haemaccel'), alginate, hydroxyethyl starch (hetastarch), polyethylene glycol, polycarboxylated polyethylene glycol, chondroitin-6-sulfate, chondroitin-4-sulfate, keratin, keratin sulfate, heparan sulfate, dermatin, dermatan sulfate, carboxymethylcellulose, heparin, dextran, or hyaluronic acid.

In one embodiment of the invention, the lipid moiety is either phosphatidic acid, an acyl glycerol, monoacylglycerol, diacylglycerol, triacylglycerol, sphingosine, sphingomyelin, chondroitin-4-sulphate, chondroitin-6-sulphate, ceramide, phosphatidylethanolamine, phosphatidylserine, phosphatidylcholine, phosphatidylinositol, or phosphatidylglycerol, or an ether or alkyl phospholipid derivative thereof, and the physiologically acceptable monomer or polymer moiety is either aspirin, lactobionic acid, maltose, glutaric acid, polyethylene glycol, carboxymethylcellulose, heparin, dextran, hemacell, hetastarch, or hyaluronic acid.

In one embodiment, the present invention provides for use of a lipid moiety bonded to a physiologically acceptable monomer, dimer, oligomer, or polymer, in the preparation of a pharmaceutical composition for treating a subject afflicted with chronic rhinosinusitis, nasal polyps, asthma, allergic rhinitis, chronic obstructive pulmonary disease, obstructive respiratory disease, colitis, Crohn's disease, central nervous system insult, multiple sclerosis, contact dermatitis, psoriasis, cardiovascular disease, including prophylaxis for invasive procedures, invasive cellular proliferative disorders, anti-oxidant therapy, hemolytic syndromes, sepsis, acute respiratory distress syndrome, tissue transplant rejection syndromes, autoimmune disease, viral infection, and hypersensitivity conjunctivitis.

In one embodiment, the present invention provides use of a pharmaceutical composition according to the present invention for treating a subject afflicted with chronic rhinosinusitis, nasal polyps, asthma, allergic rhinitis, chronic obstructive pulmonary disease, obstructive respiratory disease, colitis, Crohn's disease, central nervous system insult, multiple sclerosis, contact dermatitis, psoriasis, cardiovascular disease, including prophylaxis for invasive procedures, invasive cellular proliferative disorders, anti-oxidant therapy, hemolytic syndromes, sepsis, acute respiratory distress syndrome, tissue transplant rejection syndromes, autoimmune disease, viral infection, or hypersensitivity conjunctivitis, wherein the composition is prepared for administration by topical, oral, nasal, aerosol, intravenous, intraocular, intra-arterial, subcutaneous, or suppository routes.

In one embodiment, the invention provides a method of treating a subject suffering from a disease involving the production and/or action of lipid mediators and/or impairment of glycosaminoglycan (GAG) functioning.

In one embodiment of the invention, the physiologically acceptable monomer may be, inter alia, a salicylate, salicylic acid, aspirin, a monosaccharide, lactobionic acid, glucoronic acid, maltose, amino acid, glycine, carboxylic acid, acetic acid, butyric acid, dicarboxylic acid, glutaric acid, succinic acid, fatty acid, dodecanoic acid, didodecanoic acid, bile acid, cholic acid, cholesterylhemmisuccinate, or wherein the physiologically acceptable dimer or oligomer may be, inter alia, a dipeptide, a disaccharide, a trisaccharide, an oligosaccharide, an oligopeptide, or a di- or trisaccharide monomer unit of glycosaminoglycans, hyaluronic acid, heparin, heparan sulfate, keratin, keratan sulfate, chondroitin, chondroitin sulfate, chondroitin-4-sulfate, chondroitin-6-sulfate, dermatin, dermatan sulfate, dextran, polygeline, alginate, hydroxyethyl starch, ethylene glycol, or carboxylated ethylene glycol, or wherein the physiologically acceptable polymer may be, inter alia, a glycosaminoglycan, hyaluronic acid, heparin, heparan sulfate, chondroitin, chondroitin sulfate, keratin, keratan sulfate, dermatin, dermatan sulfate, carboxymethylcellulose, dextran, polygeline, alginate, hydroxyethyl starch, polyethylene glycol or polycarboxylated polyethylene glycol.

In another embodiment, the physiologically acceptable polymer may be, inter alia, hyaluronic acid.

In another embodiment, the physiologically acceptable polymer may be, inter alia, chondroitin sulfate.

In one embodiment of the invention, the lipid or phospholipid moiety may be, inter alia, phosphatidic acid, an acyl glycerol, monoacylglycerol, diacylglycerol, triacylglycerol, sphingosine, sphingomyelin, ceramide, phosphatidylethanolamine, phosphatidylserine, phosphatidylcholine, phosphatidylinositol, phosphatidylglycerol, or an ether or alkyl phospholipid derivative thereof.

In another embodiment, the phospholipid moiety may be, inter alia, phosphatidylethanolamine Dosages and Routes of Administration The methods of this invention can be adapted to use of the therapeutic compositions comprising Lipid-conjugates in admixture with conventional excipients, i.e. pharmaceutically acceptable organic or inorganic carrier substances suitable for parenteral, enteral (e.g., oral) or topical application which do not deleteriously react with the active compounds. Suitable pharmaceutically acceptable carriers include but are not limited to water, salt solutions, alcohols, gum arabic, vegetable oils, benzyl alcohols, polyethylene glycols, gelatine, carbohydrates such as lactose, amylose or starch, magnesium stearate, talc, silicic acid, viscous paraffin, white paraffin, glycerol, alginates, hyaluronic acid, collagen, perfume oil, fatty acid monoglycerides and diglycerides, pentaerythritol fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds. They can also be combined where desired with other active agents, e.g., vitamins.

In one embodiment, the invention provides a pharmaceutical composition for treating a subject suffering from chronic rhinosinusitis, including a lipid or phospholipid moiety bonded to a physiologically acceptable monomer, dimer, oligomer, or polymer; and a pharmaceutically acceptable carrier or excipient.

In another embodiment, the invention provides a pharmaceutical composition for preventing chronic rhinosinusitis in a subject, including a lipid or phospholipid moiety bonded to a physiologically acceptable monomer, dimer, oligomer, or polymer; and a pharmaceutically acceptable carrier or excipient.

In another embodiment, the invention provides a pharmaceutical composition for treating a subject suffering from nasal polyps, including a lipid or phospholipid moiety bonded to a physiologically acceptable monomer, dimer, oligomer, or polymer; and a pharmaceutically acceptable carrier or excipient.

In another embodiment, the invention provides a pharmaceutical composition for preventing nasal polyps in a subject, including a lipid or phospholipid moiety bonded to a physiologically acceptable monomer, dimer, oligomer, or polymer; and a pharmaceutically acceptable carrier or excipient.

In another embodiment, the invention provides a pharmaceutical composition for treating a subject suffering from chronic rhinosinusitis, including a lipid or phospholipid moiety bonded to a physiologically acceptable carrier or excipient.

In another embodiment, the invention provides a pharmaceutical composition for preventing chronic rhinosinusitis in a subject, including any one of the compounds according to the invention or any combination thereof; and a pharmaceutically acceptable carrier or excipient.

In another embodiment, the invention provides a pharmaceutical composition for treating a subject suffering from nasal polyps, including any one of the compounds according to the invention or any combination thereof; and a pharmaceutically acceptable carrier or excipient. In another embodiment, the invention provides a pharmaceutical composition for preventing nasal polyps in a subject, including any one of the compounds according to the invention or any combination thereof; and a pharmaceutically acceptable carrier or excipient.

In another embodiment, the compounds according to the invention include, inter alia, the compounds represented by the structures of the general formulae: (A), (I), (II), (III), (IV), (V), (VI), (VII), (VIII), (IX), (IXa), (IXb), (X), (XI), (XII), (XIII), (XIV), (XV), (XVI), (XVII), (XVIII), (XIX), (XX), (XXI), (XXII) or any combination thereof.

While the examples provided herein describe use of the PL conjugates in subcutaneous, intraperitoneal or topical administration, the success described affords good evidence to suppose that other routes of administration, or combinations with other pharmaceutical preparations, would be at least as successful. The route of administration (e.g., topical, parenteral, enteral, intravenous, vaginal, inhalation, nasal aspiration (spray), suppository or oral) and the dosage regimen will be determined by skilled clinicians, based on factors such as exact nature of the condition being treated, the severity of the condition, the age and general physical condition of the patient, and so on.

In general, the doses utilized for the above described purposes will vary, but will be in an effective amount to exert the desired anti-disease effect. As used herein, the term "pharmaceutically effective amount" refers to an amount of a compound of formulae A and I-XXI which will produce the desired alleviation in symptoms or signs of disease in a patient. The doses utilized for any of the above-described purposes will generally be from 1 to about 1000 milligrams per kilogram of body weight (mg/kg), administered one to four times per day, or by continuous IV infusion. When the compositions are dosed topically, they will generally be in a concentration range of from 0.1 to about 10% w/v, administered 1-4 times per day.

As used herein, the term "pharmaceutically acceptable carrier" refers to any formulation which is safe, and provides the appropriate delivery for the desired route of administration of an effective amount of at least one compound of the present invention. As such, all of the above-described formulations of the present invention are hereby referred to as "pharmaceutically acceptable carriers." This term refers to as well the use of buffered formulations wherein the pH is maintained at a particular desired value, ranging from pH 4.0 to pH 9.0, in accordance with the stability of the compounds and route of administration.

For parenteral application, particularly suitable are injectable, sterile solutions, preferably oily or aqueous solutions, as well as suspensions, emulsions, or implants, including suppositories. Ampoules are convenient unit dosages.

For application by inhalation, particularly for treatment of airway obstruction or congestion, solutions or suspensions of the compounds mixed and aerosolized or nebulized in the presence of the appropriate carrier.

For topical application, particularly for the treatment of skin diseases such as contact dermatitis or psoriasis, admixture of the compounds with conventional creams or delayed release patches is acceptable.

For enteral application, particularly suitable are tablets, dragees, liquids, drops, suppositories, or capsules. A syrup, elixir, or the like can be used when a sweetened vehicle is employed. When indicated, suppositories or enema formulations may be the recommended route of administration.

Sustained or directed release compositions can be formulated, e.g., liposomes or those wherein the active compound is protected with differentially degradable coatings, e.g., by microencapsulation, multiple coatings, etc. It is also possible to freeze-dry the new compounds and use the lyophilisates obtained, for example, for the preparation of products for injection.

Thus, the present invention provides for use of the Lipid-conjugates in various dosage forms suitable for aerosol, rectal, vaginal, conjunctival, intravenous, intra-arterial, and sublingual routes of administration.

It will be appreciated that the actual preferred amounts of active compound in a specific case will vary according to the specific compound being utilized, the particular compositions formulated, the mode of application, and the particular situs and organism being treated. Dosages for a given host can be determined using conventional considerations, e.g., by customary comparison of the differential activities of the subject compounds and of a known agent, e.g., by means of an appropriate, conventional pharmacological protocol.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

The main abbreviations used in the application are:

HA=hyaluronic acid

HYPE=dipalmitoyl-phosphatidyl-ethanolamine (PE) conjugated to HA (also referred to as HyPE, HyalPE)

CSA=chondroitin sulfate A

CSAPE=PE conjugated to CSA (also referred to as CsAPE, CsaPE)

CMC=carboxymethyl cellulose

CMPE=PE conjugated to CMC

HEPPE=PE conjugated to heparin (also referred to as HepPE, HePPE)

DEXPE=PE conjugated to dextran

AsPE=PE conjugates to aspirin

HemPE=PE conjugated to Polygeline (haemaccel)

HyDMPE=dimyristoyl PE linked to HA.

Examples demonstrating the utility of lipid-conjugates in preventing and treating disease are presented in PCT/US05/06591 filed 2 Mar. 2005, U.S. patent application Ser. No. 10/989,606 filed 17 Nov. 2004 and U.S. patent application Ser. No. 10/989,607 filed 17 Nov. 2004, which are incorporated herein by reference in their entirety.

EXAMPLE 1

Figure 2:
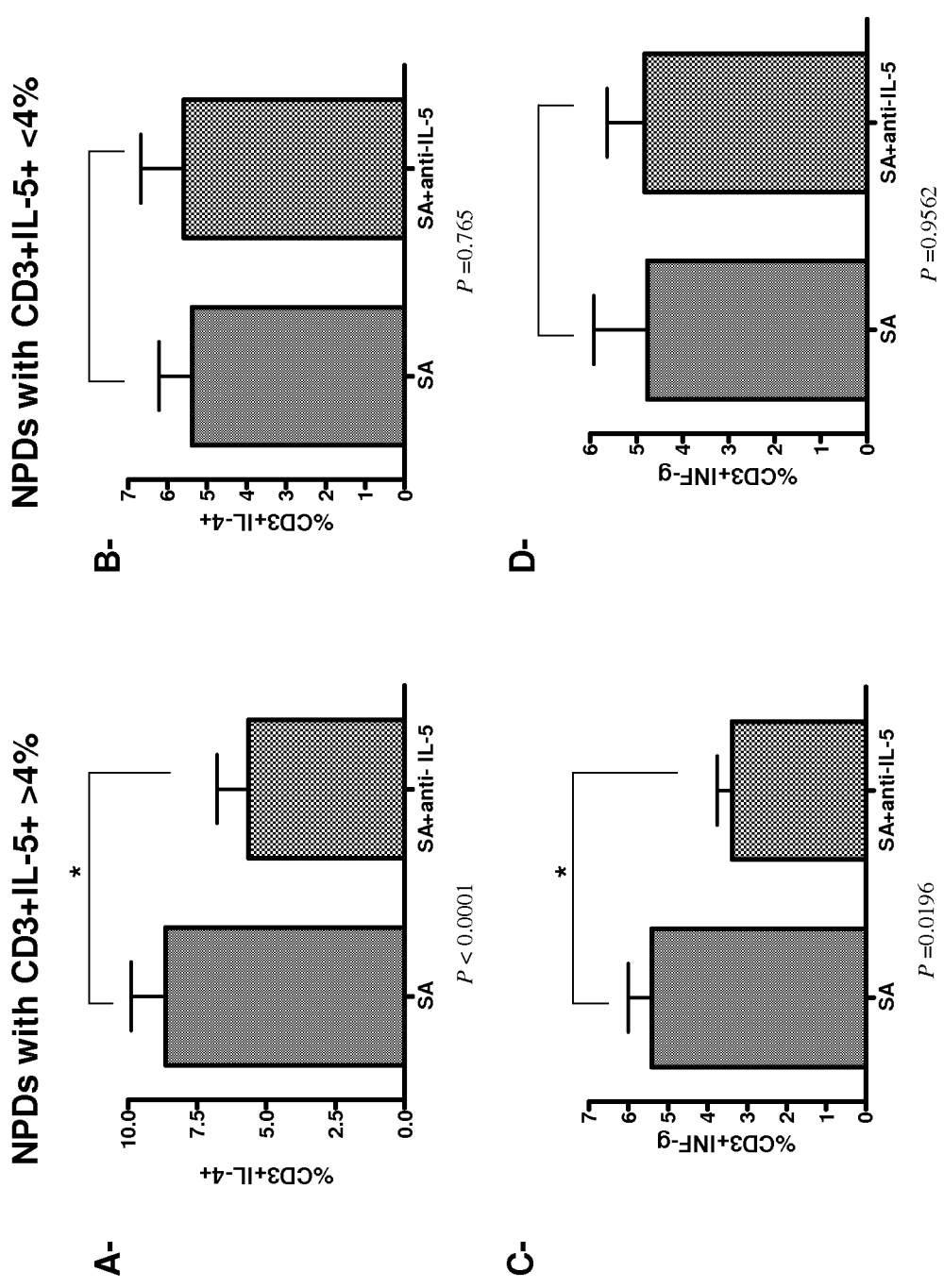
FIG. 2. Addition of anti-IL-5 antibodies to T cells from nasal polyps treated in vitro with *Staphylococcus Aureus* Superantigens (SAS) suppressed IL-4 and INF-γ release in polyps with high levels of IL-5 (A and C), while having no effect on IL-4 and INF-γ release in polyps with low levels of IL-5 (B and D).

HYPE Decreased Cytokine Levels in Nasal Polyps from Patients with Chronic Rhinosinusitis In vitro, treatment of T cells from nasal polyps with *Staphylococcus Aureus* Superantigens (SAS) induced the release of large amounts of IL-4, IL-5 and INF-γ (FIG. 1), while addition of anti-IL-5 suppressed IL-4 and INF-γ release in polyps with high amount of Th-5 (FIG. 2). Blocking the eosinophilic inflammation by anti-IL5 reduced TH1 and TH2 mediated reaction in the polyps. Similarly, in vivo studies showed that a single iv infusion of 3 mg/kg or 1 mg/kg of a humanized anti-human IL-5 monoclonal antibody in 24 patients with bilateral NP was safe, reduced eosinophil number and concentration of ECP in blood, and improved NP clinical scores in 50% of the patents receiving treatment (Gebaert et al. J Allergy Clin Immunol. 2006 November; 118(5):1133-41). Patients with high levels of basal IL-5 were more likely to be responsive to treatment with anti-IL-5 antibody.

Some findings link nasal polyp development and aggravation with the presence of specific immunologic response to SAS.

Nasal polyps were obtained from patients who underwent Endoscopic Sinus Surgery (ESS) for chronic rhinosinusitis with nasal polyps (CRSwNP) at Tel Aviv Medical Center.

Tissue was enzymatically digested, cells were filtered, and some were stimulated in vitro with SA (SA). Some groups of cells received either no treatment (NA), Hyaluronic acid-phosphtidylethanolamine (HyPE) or dexamethasone (DEXA). IL-5, IL-13, and Interferon-χ levels were measured by ELISA.

Figure 3:
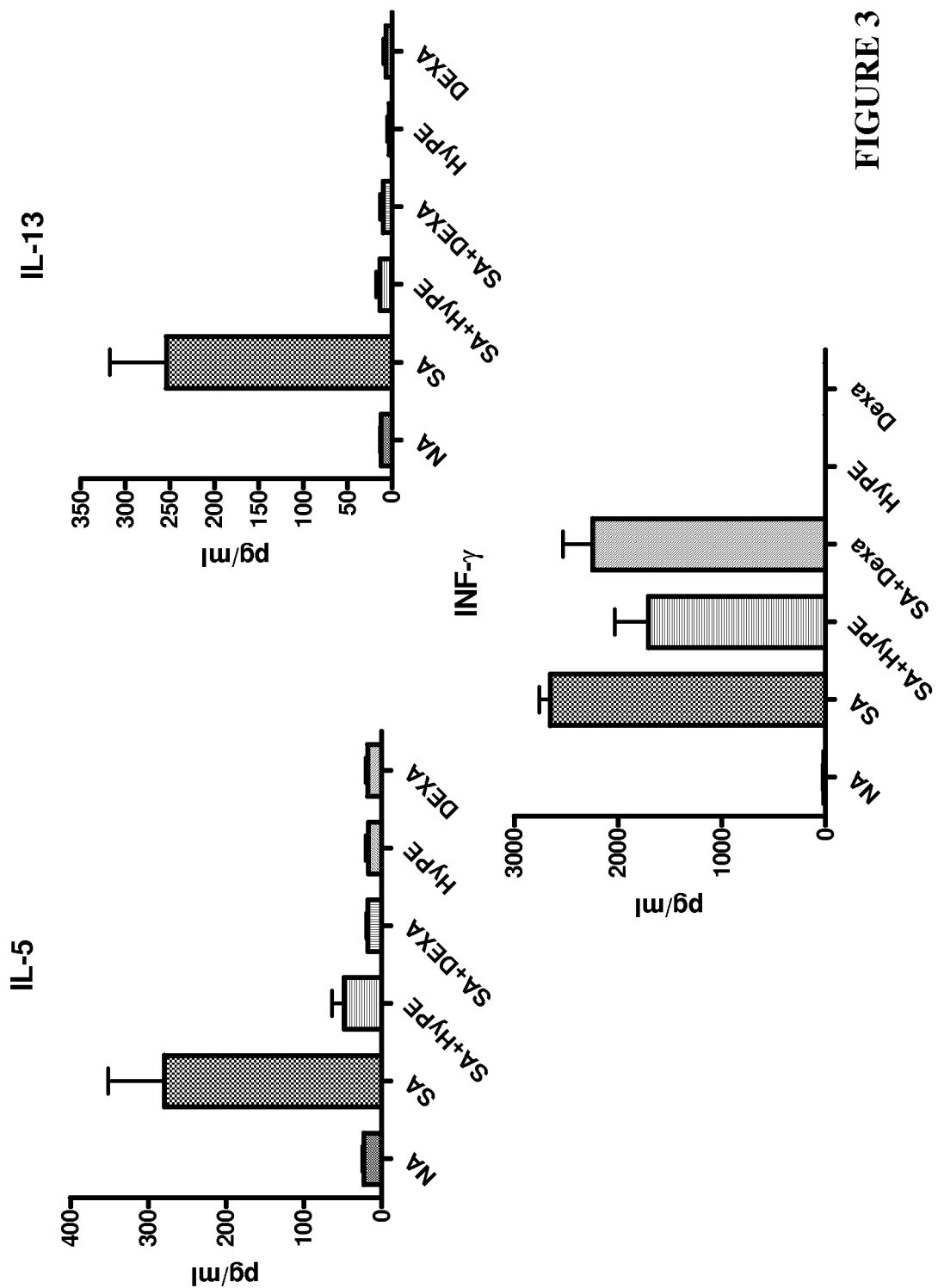
FIG. 3. Treatment of human nasal polyps with the PLA2 inhibitor HyPE, a compound of the present invention, suppressed the release of Th2 and Th1 cytokines at a level comparable to (IL-5, IL-13) or better than (Interferon-χ) that of dexamethasone.

Treatment of human nasal polyps with PLA2 inhibitor suppressed the release of Th2 and Th1 cytokines at a level comparable to (IL-5, IL-13) or better than (Interferon-χ) that of dexamethasone (FIG. 3).

EXAMPLE 2

Toxicity Tests

Experiment 2: The following compounds were tested: HyPE, CMPE, CSAPE and HepPE. The compounds were injected IP at one dose of 1000, 500 or 200 mg/Kg body weight. Toxicity was evaluated after one week, by mortality, body weight, hematocrit, blood count (red and white cells), and visual examination of internal organs after sacrifice. These were compared to control, untreated mice. Each dose was applied to a group of three mice. No significant change in the above criteria was induced by treatment with these compounds, except for the HepPE, which induced hemorrhage.

The non-toxicity of the Lipid conjugates is demonstrated in Table 2.1 and Table 2.2, depicting the results obtained for HyPE in acute (2.1) and long-term (2.2) toxicity tests.

TABLE 2.1

| | Acute toxicity | | | | |
|---|---|---|---|---|---|
| Dose of HyPE (mg/kg body weight) | Body weight (g) | | $RBC \times 10^6$ | $WBC \times 10^3$ | Hematocrit % |
| 0.0 (control) | 21.9 ± 0.2 | 22.6 ± 0.3 | 10.7 ± 0.4 | 9.3 ± 0.3 | 45.0 ± 0.5 |
| 250 | 22.1 ± 0.4 | 23.1 ± 0.6 | 11.4 ± 0.1 | 7.7 ± 0.2 | 43.3 ± 0.7 |
| 500 | 21.4 ± 0.3 | 22.3 ± 0.4 | 11.5 ± 0.3 | 8.1 ± 1.3 | 44.7 ± 2.3 |
| 1000 | 21.7 ± 0.2 | 22.1 ± 0.2 | 10.9 ± 0.4 | 7.4 ± 0.6 | 40.3 ± 0.7 |

RBC=red blood cells. WBC=white blood cells. Each datum is mean±SEM.

For long-term toxicity test of HyPE, a group of 6 mice received a dose of 100 mg HyPE/Kg body weight, injected IP 3 times a week for 30 weeks (total of 180 mg to a mouse of 20 g). Toxicity was evaluated as for Table 4.1. No mortality, and no significant change in the above criteria was induced by this treatment, compared to normal untreated mice (see Table 4.1), as depicted in Table 2.

TABLE 2.2

| | Results at week 30: | | | |
|---|---|---|---|---|
| | Body weight (g) | $RBC \times 10^6$ | $WBC \times 10^3$ | Hematocrit % |
| Control (untreated) rats | 39.5 ± 3.1 | 10.9 ± 0.8 | 9.3 ± 0.6 | 45.0 ± 0.8 |
| HyPE- injected rats | 39.0 ± 2.7 | 11.7 ± 0.7 | 8.1 ± 15 | 43.4 ± 4.9 |

EXAMPLE 3

Synthesis Procedures

The procedures below are examples for synthesis of specific variants of the lipid-conjugates, and can be modified according to the desirable compositions (e.g., changing the molar ratio between the lipid/phospholipid and the GAG, or the GAG size).

Synthesis of low molecular weight lipid-GAG conjugates are prepared according to US publication 2011-0130555 which is incorporated herein by reference.

I. HyPE=Phosphatidyl-Ethanolamine (PE)-Linked Hyaluronic Acid.

A. Truncating Hyaluronic Acid (HA):
Dissolve 20 g of HA in 12 L water, add 200 mg $FeSO_4 \cdot 7H_2O$ dissolved in 20 ml water, add 400 ml $H_2O_2$ (30%), stir for 1.5 h. Filter through 30 kD Filtron, Lyophilize Yield: 16 g truncated HA.

B. Conjugation with PE (Adjusted for 1 g):
Prepare:
1. 10 g HA dissolved in 500 ml MES buffer, 0.1M, pH=6.5
2. 1.0 g PE dissolved in 500 ml t-BuOH with 100 ml $H_2O$.

Mix the two solutions, add 1 g HOBT and 10 g EDC. Sonicate the mixture in an ultrasonic bath for 3 h. Remove access free PE (and EDC and HOBT) by extraction into organic phase (by addition of chloroform and methanol to obtain a ratio of $C/M/H_2O:1/1/1$). Separate the aqueous phase by a separation funnel. Repeat this step twice. For final cleaning from reagents, filter through a Filtron membrane (30 kD), and lyophilize.

Yield: about 8 g.

II. CSAPE=PE-Linked Chondroitin Sulfate A (CSA):
Prepare:
1. 10 g CSA dissolved in 1.2 L MES buffer, 0.1M, pH=6.5
2. 1 g PE dissolved in 120 ml chloroform/methanol: 1/1.

Add 15 ml of a detergent (DDAB).

Mix 1 with 2, while stirring, add 1 g HOBT and 10 g EDC, continue stiffing thoroughly for a day at least. Remove access free PE (and EDC and HOBT) by extraction into organic phase (by addition of chloroform and methanol to obtain a ratio of $Chloroform/MeOH/EtOH/H_2O:1/1/0.75/1$). Separate the aqueous phase by a separation funnel. Repeat this step twice. Filter through a Filtron membrane (30 kD), and lyophilize. To remove DDAB traces, dissolve 1 g of dry product in 100 ml water and 100 ml MeOH, and clean by ion exchanger using IR120 resin. Dialyse (to remove MeOH) and lyophilize Yield: about 8 g.

Unexpected results showed that the sonication applied in the HyPE synthesis, is an better substitute for the detergent in mixing the aqueous and lipid phases. Using sonication techniques simplifies the synthesis and improves the purification of the product.

It will be appreciated by persons skilled in the art that the present invention is not limited by what has been particularly shown and described herein above and that numerous modifications, all of which fall within the scope of the present invention, exist. Rather, the scope of the invention is defined by the claims which follow:

What is claimed is:

1. A method of treating or preventing chronic rhinosinusitis in a subject, comprising the step of administering to said subject a compound represented by the structure of the general formula (A):

$$[\text{L}-\text{Z}-\text{Y}]_n-\text{X} \qquad (A)$$

wherein
L is a phospholipid;
Z is nothing;
Y is nothing;
X is a glycosaminoglycan; and
n is a number from 1 to 1000.

2. The method according to claim 1 wherein said glycosaminoglycan is selected from the group consisting of hyaluronic acid, heparin, heparin sulfate, chondroitin, chondroitin sulfate, keratan, keratan sulfate, and dermatan sulfate or a derivative thereof.

3. The method according to claim 1, wherein L is phosphatidylethanolamine.

4. The method according to claim 3, wherein said phosphatidylethanolamine is dipalmitoyl phosphatidylethanolamine.

5. The method according to claim 1, wherein said chronic rhinosinusitis is chronic rhinosinusitis with polyps.

6. A method of treating or preventing nasal polyps in a subject, comprising the step of administering to said subject a compound represented by the structure of the general formula (A):

$$[\text{L}-\text{Z}-\text{Y}]_n-\text{X} \qquad (A)$$

wherein
L is a phospholipid;
Z is nothing;
Y is nothing;
X is a glvcosaminoglycan; and
n is a number from 1 to 1000.

7. The method according to claim 6, wherein said glycosaminoglycan is selected from the group consisting of hyaluronic acid, heparin, heparin sulfate, chondroitin, chondroitin sulfate, keratan, keratan sulfate, and dermatan sulfate or a derivative thereof.

8. The method according to claim 6, wherein L is a phosphatidylethanolamine.

9. The method according to claim 8, wherein said phosphatidylethanolamine is dipalmitoyl phosphatidylethanolamine.

10. The method according to claim 1, wherein said compound is represented by the structure of the general formula (I):

$$\left[ \begin{array}{c} R_1-\overset{O}{\underset{\|}{C}}-O-\overset{H}{\underset{|}{C}}-H \\ R_2-\overset{O}{\underset{\|}{C}}-O-\overset{H}{\underset{|}{C}}-H \quad O \quad H \quad H \quad H \\ O \quad H-\overset{H}{\underset{|}{C}}-O-\overset{\|}{\underset{O^-}{P}}-O-\overset{H}{\underset{|}{C}}-\overset{H}{\underset{|}{C}}-N-Y \end{array} \right]_n - X \qquad (I)$$

wherein
$R_1$ is a linear, saturated, mono-unsaturated, or poly-unsaturated, alkyl chain ranging in length from 2 to 30 carbon atoms;
$R_2$ is a linear, saturated, mono-unsaturated, or poly-unsaturated, alkyl chain ranging in length from 2 to 30 carbon atoms;
Y is nothing;
X is glycosaminoglycan; and
n is a number from 1 to 1,000.

11. The method of claim 10, wherein said glycosaminoglycan is selected from the group consisting of hyaluronic acid, heparin, heparin sulfate, chondroitin, chondroitin sulfate, keratan, keratan sulfate, dermatan sulfate or a derivative thereof.

12. The method of claim 1, wherein said glycosaminoglycan has a molecular weight of between 5 kD and 90 kD.

13. The method of claim 1, wherein said glycosaminoglycan has a molecular weight of between 5 kD and 20 kD.

14. The method according to claim 6, wherein said compound is represented by the structure of the general formula (I):

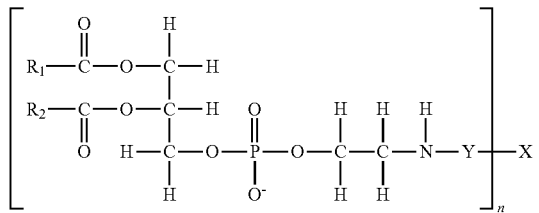

wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Y is nothing;

X is glycosaminoglycan; and n is a number from 1 to 1,000.

15. The method of claim 14, wherein said glycosaminoglycan is selected from the group consisting of hyaluronic acid, heparin, heparin sulfate, chondroitin, chondroitin sulfate, keratan, keratan sulfate, dermatan sulfate or a derivative thereof.

16. The method of claim 14, wherein said glycosaminoglycan has a molecular weight of between 5 kD and 20 kD.

17. The method of claim 10, wherein n is a number from 2 to 500.

18. The method of claim 14, wherein n is a number from 2 to 500.

19. The method of claim 1, wherein the step of administering comprises nasal administration.

20. The method of claim 6, wherein the step of administering comprises nasal administration.

* * * * *